United States Patent
Naber et al.

(10) Patent No.: US 11,771,322 B2
(45) Date of Patent: Oct. 3, 2023

(54) COMPUTER-IMPLEMENTED METHOD, COMPUTER PROGRAM AND SURGICAL SYSTEM FOR DETERMINING THE VOLUMETRIC FLOW RATE OF BLOOD THROUGH A PORTION OF A BLOOD VESSEL IN A SURGICAL FIELD

(71) Applicant: CARL ZEISS MEDITEC AG, Jena (DE)

(72) Inventors: Ady Naber, Karlsruhe (DE); Werner Nahm, Bühlerzell (DE); Christoph Hauger, Aalen (DE); Roland Guckler, Ulm (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 17/793,805

(22) PCT Filed: Feb. 2, 2021

(86) PCT No.: PCT/EP2021/052449
§ 371 (c)(1),
(2) Date: Jul. 19, 2022

(87) PCT Pub. No.: WO2021/156266
PCT Pub. Date: Aug. 12, 2021

(65) Prior Publication Data
US 2023/0080925 A1    Mar. 16, 2023

(30) Foreign Application Priority Data
Feb. 3, 2020    (DE) ...................... 10 2020 102 681.1

(51) Int. Cl.
*A61B 5/1455*    (2006.01)
*A61B 5/00*    (2006.01)
(Continued)

(52) U.S. Cl.
CPC .......... *A61B 5/0071* (2013.01); *A61B 5/0261* (2013.01); *G06V 10/255* (2022.01);
(Continued)

(58) Field of Classification Search
CPC ......... A61B 5/02; A61B 5/1455; A61B 5/028; A61B 5/0071; A61B 5/0059
See application file for complete search history.

(56) References Cited

U.S. PATENT DOCUMENTS

2007/0244393 A1    10/2007    Oshiki et al.
2012/0190967 A1    7/2012    Nahm

FOREIGN PATENT DOCUMENTS

| DE | 600 38 730 T2 | 7/2009 |
|---|---|---|
| DE | 10 2010 055 772 A1 | 6/2012 |
| EP | 3047796 A1 | 7/2016 |

OTHER PUBLICATIONS

Tsukiyama et al., "Optical effects on the surrounding structure during quantitative analysis using indocyanine green videoangiograph: A phantom vessel study," Journal of Biophotonics, 2018, 11.—ISSN 1864-0648, pp. 1-7.
(Continued)

*Primary Examiner* — Marjan Fardanesh
(74) *Attorney, Agent, or Firm* — NIXON PEABODY LLP

(57) ABSTRACT

The invention relates to a computer-implemented method (10) for determining the blood volume flow ($I_{BJ}$) through a portion ($90_i$, i=1, 2, 3, . . . ) of a blood vessel (88) in an operating region (36) using a fluorophore. A plurality of images ($80_1$, $80_2$, $80_3$, $80_4$, . . . ) are provided, which are based on fluorescent light in the form of light having wavelengths lying within a fluorescence spectrum of the fluorophore, and which show the portion ($90_i$) of the blood vessel (88) at different recording times ($t_1$, $t_2$, $t_3$, $t_4$, . . . ). By
(Continued)

processing at least one of the provided images ($80_1$, $80_2$, $80_3$, $80_4$, ...), a diameter (D) and a length (L) of the portion ($90_i$) of the blood vessel (88) and also a time interval for a propagation of the fluorophore through the portion ($90_i$) of the blood vessel (88) are determined, which time interval describes a characteristic transit time ($\tau$) for the fluorophore in the portion ($90_i$) of the blood vessel (88), in which a blood vessel model ($M_B^Q$) for the portion ($90_i$) of the blood vessel (88) is specified, which blood vessel model describes the portion ($90_i$) of the blood vessel (88) as a flow channel (94) having a length (L), having a wall (95) with a wall thickness (d), and having a free cross section Q. A fluid flow model $M_F^Q$ for the blood vessel model ($M_B^Q$) is assumed, which fluid flow model describes a local flow velocity (122) at different positions over the free cross section Q of the flow channel (94) in the blood vessel model ($M_B^Q$), and a fluorescent light model $M_L^Q$ is assumed, which describes a spatial probability density for the intensity of the remitted light at different positions over the free cross section Q of the flow channel (94) in the blood vessel model ($M_B^Q$), which light is emitted by a fluid, which is mixed with fluorophore and flows through the free cross section Q of the flow channel (94) in the blood vessel model ($M_B^Q$), when said fluid is irradiated with fluorescence excitation light. The blood volume flow ($I_{BI}$) is determined as a fluid flow guided through the flow channel (94) in the blood vessel model ($M_B^Q$), which fluid flow is calculated from the length (L) and the diameter (D) of the portion ($90_i$) of the blood vessel (88) and from the characteristic transit time ($\tau$) for the fluorophore in the portion ($90_i$) of the blood vessel (88), using the fluid flow model $M_F^Q$ and the fluorescent light model $M_L^Q$.

16 Claims, 13 Drawing Sheets

(51) Int. Cl.
  *G06V 10/50* (2022.01)
  *G06V 10/20* (2022.01)
  *G06V 10/44* (2022.01)
  *G16H 30/40* (2018.01)
  *A61B 5/026* (2006.01)

(52) U.S. Cl.
  CPC ............ *G06V 10/446* (2022.01); *G06V 10/50* (2022.01); *G16H 30/40* (2018.01)

(56) References Cited

OTHER PUBLICATIONS

Weichelt et al., "Quantitative fluorescence angiography for neurosurgical interventions," Biomed Tech, 2013, vol. 58, No. 3, pp. 269-279.
Xu et al., "Complex-based OCT angiography algorithm recovers microvascular information superior to amplitude or phase-based algorithm in phase-stable systems." Phys. Med. Biol. vol. 63, No. 1, Dec. 19, 2018, pp. 1-29.
German Office Action for 102020102681.1, dated Jan. 26, 2021 (13 pages).
International Preliminary Report on Patentability for Application No. PCT/EP2021/052449, dated Dec. 21, 2021 (15 pages).
International Search Report for Application No. PCT/EP2021/052449, dated May 11, 2021 (6 pages).
Written Opinion for Application No. PCT/EP2021/052449, dated May 11, 2021 (20 pages).

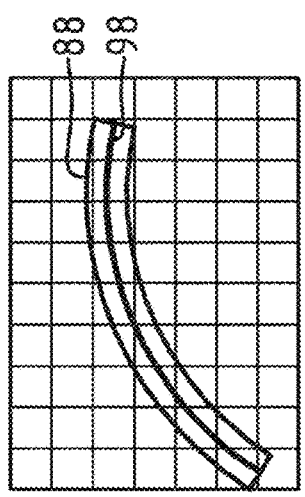
Fig.5C
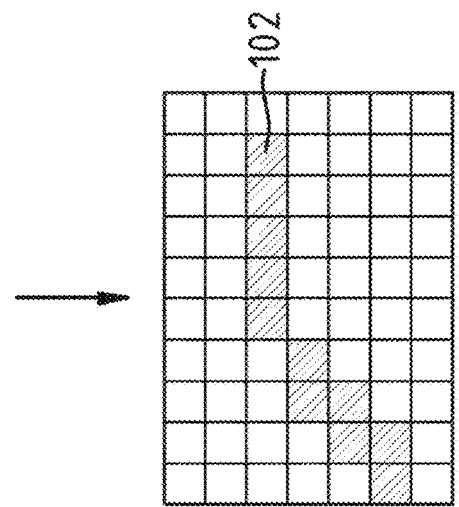
Fig.5D
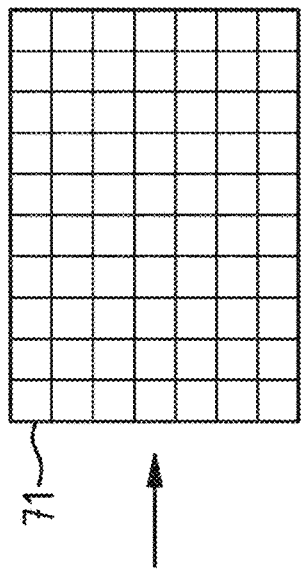
Fig.5B
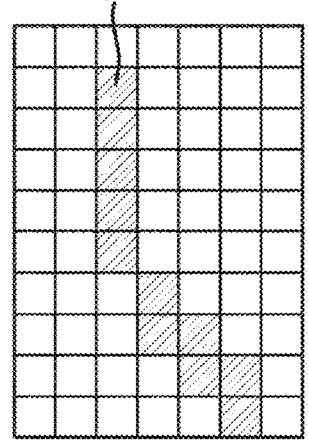
Fig.5E
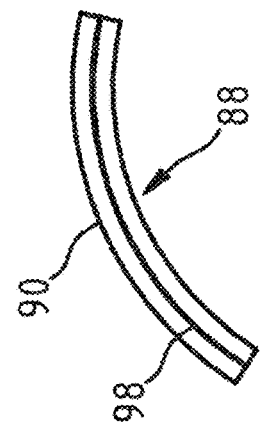
Fig.5A
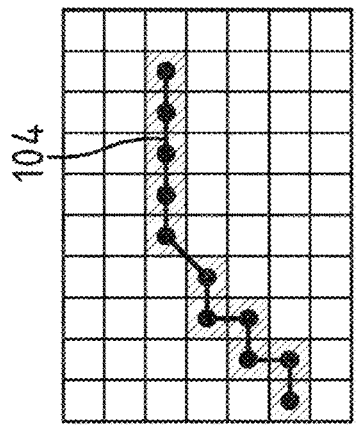
Fig.5F
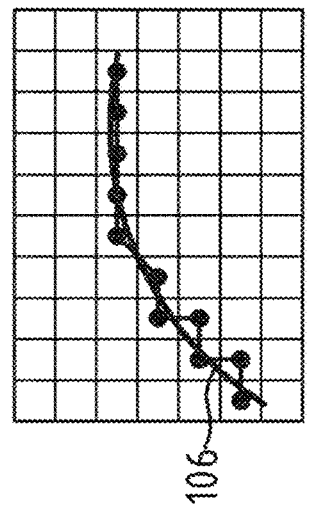

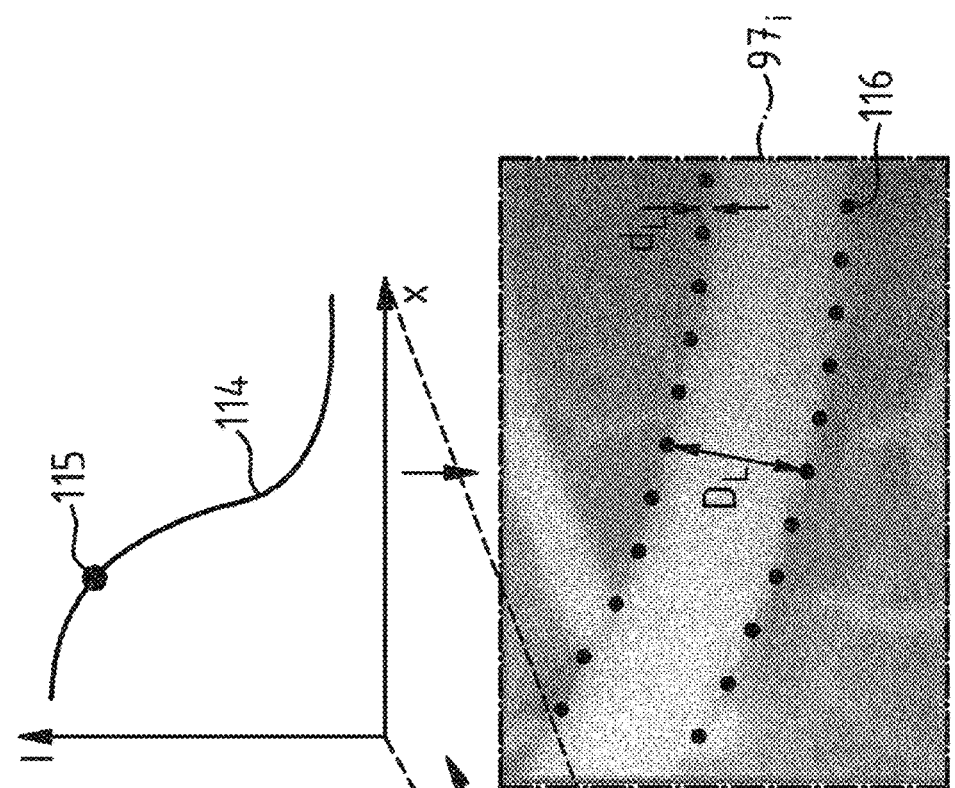
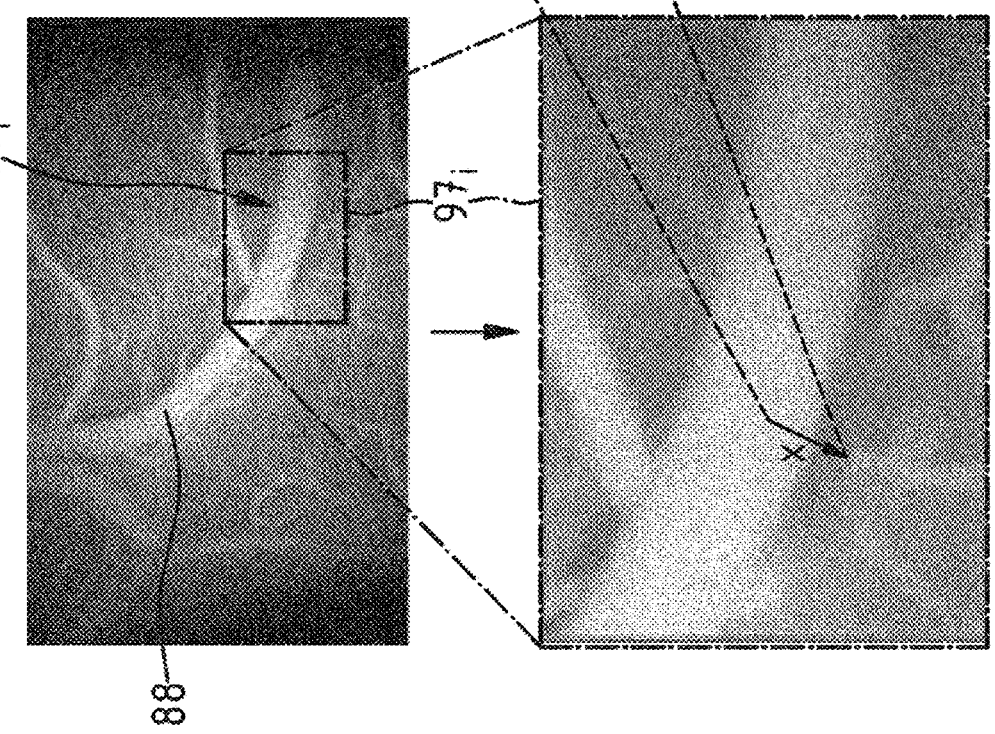

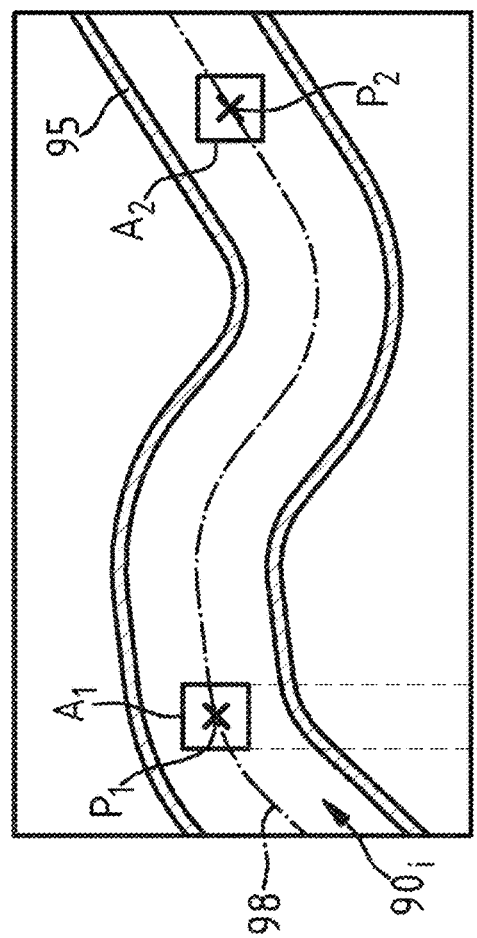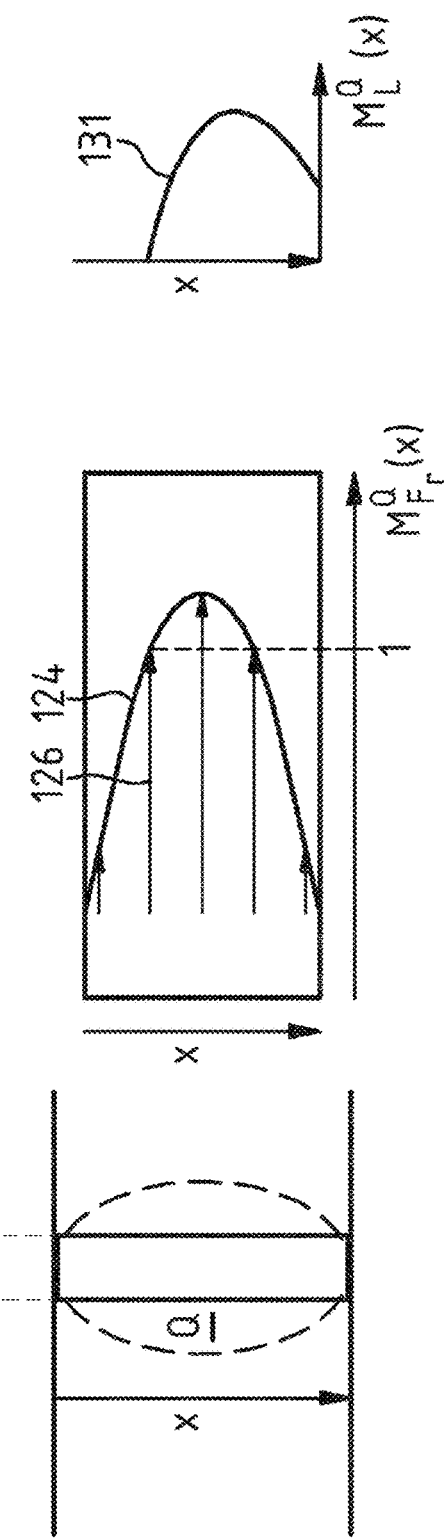
Fig.13A Fig.13B Fig.13C Fig.13D

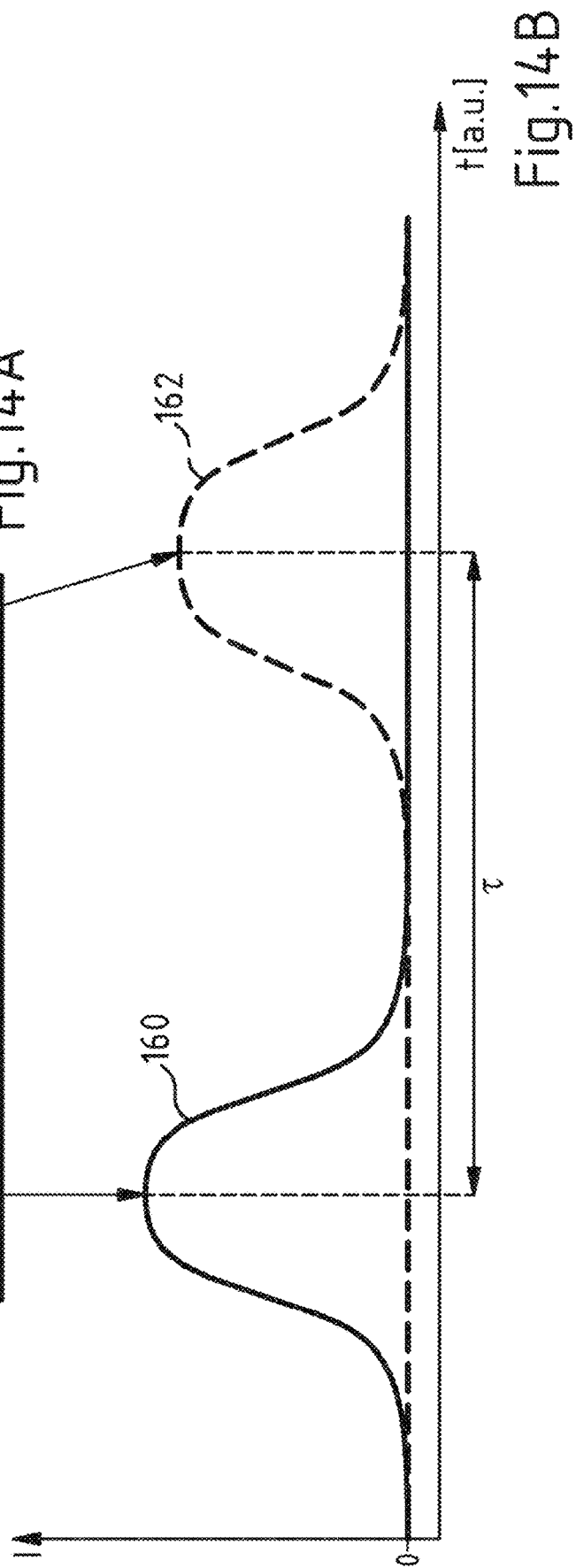

COMPUTER-IMPLEMENTED METHOD, COMPUTER PROGRAM AND SURGICAL SYSTEM FOR DETERMINING THE VOLUMETRIC FLOW RATE OF BLOOD THROUGH A PORTION OF A BLOOD VESSEL IN A SURGICAL FIELD

CROSS-REFERENCE TO RELATED APPLICATIONS

The present application is the U.S. national stage entry of International Application No. PCT/EP2021/052449, filed Feb. 2, 2021, which claims the benefit of and priority to German Patent Application No. 10 2020 102 681.1, filed Feb. 3, 2020, the contents of which are incorporated by reference herein in their entirety.

The invention relates to a computer-implemented method for determining the blood volume flow through a portion of a blood vessel in an operating region using a fluorophore. In this case, a plurality of images are provided which are based on fluorescent light in the form of light having wavelengths lying within a fluorescence spectrum of the fluorophore, and which show the portion of the blood vessel at different recording times. By processing the provided images, a diameter and a length of the portion of the blood vessel and also a time interval for a propagation of the fluorophore through the blood vessel are determined, which time interval describes a characteristic transit time for the fluorophore in the blood vessel. The invention also relates to a computer program and a surgical system for determining the blood volume flow through a portion of a blood vessel in an operating region using a fluorophore.

The determination of the blood volume flow is of interest in neurosurgical operations, for example, since the success of bypass revascularization, of aneurysm clipping or of angioma treatment can be checked in this way. The movement of the plasma proteins contained in human blood can be made visible by staining the blood with a fluorescent dye, e.g. with the dye indocyanine green (ICG), which binds to plasma proteins in the blood and can be excited to fluorescence by illumination with light of a suitable wavelength. If such a fluorescent dye is fed into the bloodstream of a patient, a blood volume flow in the blood vessels of a patient can be inferred by evaluation of corresponding video images using a video camera system designed to capture the fluorescent light of the fluorescent dye.

A computer-implemented method of the type mentioned at the outset for determining the blood volume flow through a portion of a blood vessel in an operating region is known from "Claudia Weichelt et al. Quantitative fluorescence angiography for neurosurgical interventions, Biomed Tech 2013, volume 58, no. 3, pp. 269-279". The latter describes the determination of the blood volume flow in a blood vessel into which the dye ICG is fed, and for which a video sequence is recorded by means of a video camera. Here, a starting point and an end point of a portion of a blood vessel of interest are selected by a surgeon in order to determine the blood volume flow. At these points, the intensity of the fluorescent light is determined over time and smoothed, and then the time offset between the intensity curves and the length of the portion of the blood vessel is determined. A blood flow velocity is then determined from the time offset and the length, in order to use a cross section of the blood vessel to calculate a blood volume flow.

On page 274 in the section "Phantom Measurements" in "Claudia Weichelt et al. Quantitative fluorescence angiography for neurosurgical interventions, Biomed Tech 2013, volume 58, no. 3, pp. 269-279", it is mentioned that the value of the blood volume flow calculated in this publication deviates from the value measured during experiments by a factor that is dependent on the diameter of the blood vessel. However, no rule is given for the calculation of this factor.

In "Tsukiyama, A.; Murai, Y.; Matano, F.: Shirokane, K.; Morita, A.: Optical effects on the surrounding structure during quantitative analysis using indocyanine green videoangiography: A phantom vessel study, J. Biophotonics, 2018, 11.-ISSN 1864-0648", it is described how the local intensity of fluorescent light, which is detected by means of a surgical microscope from an observation window in an operating region with a blood vessel, is dependent not only on the distance of the observation window to the blood vessel, but also on the thickness of the blood vessel and on the spatial environment of the blood vessel. It is pointed out there that this dependency must be taken into account in a quantitative analysis of fluorescent light in order to infer the blood flow in a blood vessel.

"Xu, J., Song, S., Li, Y., and Wang, R.: Complex-based OCT angiography algorithm recovers microvascular information superior to amplitude or phase-based algorithm in phase-stable systems, Physics in medicine and biology, vol. 63, 19 Dec. 2017, 1-ISSN 1361-6560" specifies the examination of the retina using OCT in order in particular to visualize blood vessels there by evaluating the phase and amplitude of the OCT signal.

"Saito et al., Quantitative Blood Flow Assessment by Multiparameter Analysis of Indocyanine Green Video Angiography, World Neurosurgery, 2018, volume 116, pp. 187-193" discloses an analysis of several measurable variables in the video data when ICG is added and the operating region is irradiated with fluorescence excitation light. Here, the intensity profile over time is examined at just one point of the blood vessel and, by comparison with an experiment, the gradient is found to be the best indicator for the blood volume flow. However, a specific calculation rule for determining the blood volume flow during an operation is not specified.

The object of the invention is to permit, particularly in a surgical operation, an exact determination of the blood volume flow through a portion of a blood vessel of a patient.

This object is achieved by the method specified in claim 1 for determining the blood volume flow through a portion of a blood vessel, by the computer program specified in claim 14, and by the device specified in claim 15. Advantageous embodiments and developments of the invention are set forth in the dependent claims.

In the present case, the term blood volume flow $I_{Bi}$ denotes the volume V of the blood that flows per unit of time t through the portion of the blood vessel with diameter D and length L:

$$I_{Bi} = \dot{V} = \left(\frac{D}{2}\right)^2 \pi \frac{L}{t} = \left(\frac{D}{2}\right)^2 \pi v$$

where $$v := \frac{L}{t}.$$

The computer-implemented method according to the invention, specified in claim 1, for determining the blood volume flow through a portion of a blood vessel in an operating region using a fluorophore comprises the following method steps:

A plurality of images are provided which are based on fluorescent light in the form of light having wavelengths lying within a fluorescence spectrum of the fluorophore, and which show the portion of the blood vessel at different successive recording times. By processing the provided images, a diameter and a length of the portion of the blood vessel and also a time interval for a propagation of the fluorophore through the portion of the blood vessel are determined, which time interval describes a characteristic transit time for the fluorophore in the portion of the blood vessel. A blood vessel model which describes the portion of the blood vessel as a flow channel having a length, having a wall with a wall thickness, and having a free cross section Q is adapted to at least one of the provided images by means of image processing. A fluid flow model $M_F^Q$ for the adapted blood vessel model is provided which describes a local flow velocity at different positions over the free cross section Q of the flow channel in the adapted blood vessel model. Moreover, a fluorescent light model $M_L^Q$ is provided which describes a spatial probability density for the intensity of the remitted light at different positions over the free cross section Q of the flow channel in the adapted blood vessel model, which light is emitted by a fluid, which is mixed with fluorophore and flows through the free cross section Q of the flow channel in the adapted blood vessel model, when said fluid is irradiated with fluorescence excitation light. Moreover, a blood volume flow is determined as a fluid flow guided through the flow channel in the adapted blood vessel model, which fluid flow is calculated from the length and diameter of the portion of the blood vessel and also from the characteristic transit time of the fluorophore in the portion of the blood vessel, using the fluid flow model $M_F^Q$ provided and the fluorescent light model $M_L^Q$ provided.

For the portion of the blood vessel, a blood vessel model $M_B^Q$ is processed which describes the portion of the blood vessel as a flow channel having a length, having a wall with a wall thickness and having a free cross section Q, by at least one of the provided images being processed. Moreover, a fluid flow model $M_F^Q$ for the blood vessel model $M_B^Q$ is processed which describes a local flow velocity at different positions over the free cross section Q of the flow channel in the blood vessel model $M_B^Q$. In addition, a fluorescent light model $M_L^Q$ is assumed which describes a spatial probability density for the intensity of the remitted light at different positions over the free cross section Q of the flow channel in the blood vessel model $M_B^Q$, which light is emitted by a fluid, which is mixed with fluorophore and flows through the free cross section Q of the flow channel in the blood vessel model $M_B^Q$, when said fluid is irradiated with fluorescent light. Finally, the blood volume flow is determined as a fluid flow guided through the flow channel in the blood vessel model $M_B^Q$, which fluid flow is calculated from the length and diameter of the portion of the blood vessel and also from the characteristic transit time for the fluorophore in the portion of the blood vessel, using the fluid flow model $M_F^Q$ and the fluorescent light model $M_F^Q$.

The fluid flow model $M_F^Q$ denotes a mapping of the free cross section Q, in particular of partial regions of the latter, to flow velocities, wherein the flow velocities can be specified one-dimensionally in the form of the amount of the flow velocity or in the form of an n-dimensional flow velocity vector with amount and direction:

$$M_F^Q: Q \to \mathbb{R}^n, n \in \mathbb{N}.$$

The fluorescent light model $M_L^Q$ denotes a mapping of the free cross section Q, in particular of partial regions of the latter, to a real number:

$$M_L^Q: Q \to \mathbb{R}.$$

Meeting the model assumptions based on the blood vessel model $M_B^Q$, the fluid flow model $M_F^Q$ and the fluorescent light model $M_L^Q$ enables the blood volume flow through the portion of the blood vessel to be determined from the images provided during the operation, using a specific calculation rule. As a result, the method can be used in practice during an operation. On account of the different parameters of the model assumptions, the method for determining the blood volume flow can be flexibly adapted to different scenarios. The method is therefore also suitable for measuring the volume flow of a medium other than blood through a vessel with a different layer structure, the medium having a characteristic fluid flow and the fluorescent light having characteristic properties which can be represented in the model assumptions. By adapting the model assumptions to the specific circumstances during operations, an increased accuracy of the blood volume flow determined using the method can also be achieved.

The method according to the invention is based on the following assumptions: The portion of the blood vessel under consideration is clearly and completely visible in the provided images and is located in the focal plane of the image acquisition device. The parameters of the image acquisition device and also the parameters of the blood vessel model $M_B^Q$, of the fluid flow model $M_F^Q$ and of the fluorescent light model $M_L^Q$ are not changed during the determination of the blood volume flow.

It is advantageous if the blood vessel model $M_B^Q$ is a hollow cylinder with the length determined for the portion of the blood vessel, with the determined diameter and with the determined wall thickness. This simplifies the blood vessel model $M_B^Q$ and thus also the calculation of the blood volume flow, as a result of which computing time can be saved.

Furthermore, it is advantageous if the fluid flow model $M_F^Q$ describes a laminar fluid flow through the flow channel of the blood vessel model $M_B^Q$. This measure simplifies the fluid flow model $M_F^Q$ and thus also the calculation of the blood volume flow, as a result of which computing time can likewise be saved.

In order to determine the blood volume flow through the portion of the blood vessel, it is also advantageous if the fluid flow model $M_F^Q$ and the fluorescent light model $M_L^Q$ describe a local sector of the blood vessel model $M_B^Q$, such that the archetype of the fluid flow model $M_F^Q$ and of the fluorescent light model $M_L^Q$ corresponds to a partial region of the free cross section Q of the blood vessel model $M_B^Q$. This in turn simplifies the method and makes the latter applicable in practice. In particular, it is helpful if the fluid flow model $M_F^Q$ and the fluorescent light model $M_L^Q$ are defined, not on the free cross section Q, but instead only on the diameter of the free cross section Q along a line which runs orthogonal to the center line of the blood vessel and which intersects the center line. Every point $x \in D \subset Q$ then corresponds to a penetration depth of photons into the blood vessel.

The fluorescent light model $M_L^Q$ is preferably based on an in silico simulation of an irradiation of the blood vessel model $M_B^Q$ with fluorescence excitation light, where photons are assumed to be particles scattered at scattering centers. The scattering centers in the flow channel and in the wall of the blood vessel model $M_B^Q$ each have a characteristic scattering center distribution. The blood vessel model $M_B^Q$ is represented as a layer model with three layers: blood vessel wall—flow channel—blood vessel wall. The movement of a large number of photons is simulated in this layer model using previously defined parameters for the absorption, scattering and scattering anisotropy of the photons in the medium within the layers and at layer boundaries, as described in the publication "L. Wang, S. Jacques, "Monte Carlo Modeling of Light Transport in Multi-layered Tissues in Standard C, Computer Methods and Programs in Biomedicine, vol. 47, no. 2, pp. 131-146, 1995", to which reference is hereby made in full and the disclosure of which is included in the description of this invention. In order to determine the fluorescent light model $M_L^Q$ using the in silico simulation, it is advantageous if the archetype of the fluorescent light model $M_L^Q$ corresponds to a chord of the free cross section Q of the blood vessel model $M_B^Q$, which chord represents the penetration depth of the photons into the blood vessel model $M_B^Q$ when irradiated with fluorescence excitation light. Here, a chord of a cross section Q denotes a line between any two points on the edge of the cross section Q, such that the line runs within the cross section Q. The fluorescent light model $M_L^Q$ then maps the penetration depth x onto the proportion of the photons remitted from the blood vessel model $M_B^Q$, their maximum penetration depth in the blood vessel model $M_B^Q$ corresponding to the value x during the simulation. The fluorescent light model $M_L^Q(x)$ can be understood as a probability density with $\int_Q M_L^Q(x)dx = 1.$ In an advantageous embodiment of the method, provision is made that the fluid flow model $M_F^Q$ corresponds to a relative fluid flow model $M_{Fr}^Q$, which describes a relative flow profile in the form of a relative flow velocity at different positions over the free cross section Q of the flow channel in the blood vessel model $M_B^Q$ in relation to a reference flow velocity $v_R$. The relative fluid flow model $M_{Fr}^Q$, results from the fluid flow model $M_F^Q$ as follows:

$$M_{Fr}^Q(x) := \frac{M_F^Q(x)}{v_R}, x \in Q.$$

Using a relative fluid flow model $M_{Fr}^Q$ has the advantage that the flow velocities at different positions in relation to each other and to the reference flow velocity $v_R$ are known. Thus, the observation of a velocity at a location in the blood vessel can be used to infer the reference flow velocity $v_R$. The reference flow velocity $v_R$ is selected by the user. The reference flow velocity $v_R$ can be selected for example as a flow velocity $v_x$ of the fluid flow model at a given location $x \in Q$ in the blood vessel model $M_B^Q$ with $v_x = M_F^Q(x)$ for an $x \in Q$, as a maximum flow velocity $v_{max}$ of the fluid flow model in the blood vessel model $M_B^Q$ with $v_{max} = \max\{M_F^Q(x)|x \in Q\}$, as an average flow velocity $v_{Mittel}$ of the fluid flow model in the blood vessel model $M_B^Q$ with $$v_{average} = \frac{\int_Q M_F^Q(x)dx}{\int_Q dx}.$$

Since the fluid flow model $M_F^Q$ is a relative fluid flow model $M_{Fr}^Q$ which describes a local relative flow velocity at different positions over the free cross section Q of the flow channel in the blood vessel model $M_B^Q$ in relation to a reference flow velocity $v_R$, the determination of the blood volume flow $I_{BI}$ through a portion of a blood vessel in an operating region using a fluorophore can be achieved with increased accuracy.

This measure makes it possible in fact to ascertain the error, discussed in the abovementioned publication by Claudia Weichelt et al. and determined from an experiment, in the calculation of the blood volume flow in the form of a factor for the blood volume flow determined there from the relative fluid flow model $M_{Fr}^Q$ and the fluorescent light model $M_L^Q$.

In order to improve the accuracy of the method for determining the blood volume flow, the invention proposes that the factor measured in the abovementioned publication by Claudia Weichelt et al. be determined analytically. In an advantageous development of the invention, provision is therefore made that the observed flow velocity $v_{observed}$ be corrected using a correction factor as follows:

$v_{corrected} = v_{observed} \cdot k\_v_R,$ where the correction factor $k\_v_R$ is determined according to the reference flow velocity $v_R$ of the relative fluid flow model $M_{Fr}^Q$.

The invention is based on the finding that the characteristic transit time T for the fluorophore, corresponding to the determined time interval, in the portion of a blood vessel with the diameter D and length L, which corresponds to an observed flow velocity, $$v_{observed} := \frac{L}{\tau}$$

is dependent in particular on the penetration depth of the fluorescent light into the blood vessel, because the proportion of the remitted fluorescent light changes with the penetration depth of the fluorescent light into the blood vessel. The fluorescent light model $M_L^Q$ therefore influences the flow velocity $v_{observed}$ observed in the portion of the blood vessel.

By a combination of the fluid flow model $M_F^Q$ with the fluorescent light model $M_L^Q$, the knowledge of the fluorescent light remitted from different penetration depths can be included in the calculation of the flow velocity in the blood vessel model $M_B^Q$.

The inventors have in fact recognized that the intensity of the remitted light does not correspond to a uniform distribution over all penetration depths, but rather that the proportion of the remitted light from certain penetration depths is particularly high and from other penetration depths is very low. This relationship is described by the fluorescent light model $M_L^Q$.

One finding of the invention is therefore in particular that the correction factor can be determined from the fluid flow model $M_F^Q$ and from the fluorescent light model $M_L^Q$, which are both based on the blood vessel model $M_B^Q$.

For this purpose, the flow velocity $v_{model}$ observed in the blood vessel model $M_B^Q$ as an expected value over the observed local flow velocities of the fluid flow model $M_F^Q$, according to the spatial probability density specified in the fluorescent light model $M_L^Q$ for the intensity of the remitted light at different positions over the free cross section Q of the flow channel 94 in the blood vessel model ($M_B^Q$), is calculated as follows:

$v_{model} = \int_Q M_F^Q(x) M_L^Q(x) dx.$

If the fluid flow model $M_F^Q$ corresponds to a relative fluid flow model $M_{Fr}^Q$ at a selected reference flow velocity $v_R$, then:

$$v_{model} = \int_Q (M_{Fr}^Q(x) v_R) M_L^Q(x) dx.$$

and thus $$v_R = v_{model} \frac{1}{\int_Q M_{Fr}^Q(x) \ M_L^Q(x) dx}.$$

From the flow velocity $v_{model}$ observed in the blood vessel model $M_B^Q$, the correction factor $$k\_v_R := \frac{1}{\int_Q M_{Fr}^Q(x) \ M_L^Q(x) dx}$$

can thus be used to infer the reference flow velocity $v_R$. This correction factor depends on the selected reference flow velocity $v_R$ in the fluid flow model $M_F^Q$.

Assuming that the flow velocity $v_{observed}$ actually observed in the portion of the blood vessel corresponds to the flow velocity $v_{model}$ observed in the blood vessel model $M_B^Q$, i.e.

$$v_{model} = v_{observed},$$

the flow velocity $v_{observed}$ observed in the portion of the blood vessel can be used to determine the reference flow velocity $\overline{v_R}$ to be expected in the portion of the blood vessel. The flow velocity $v_{observed}$ observed in the portion of the blood vessel is therefore corrected on the basis of the correction factor $k\_v_R$ when choosing a suitable reference flow velocity $v_R$:

$$v_{corrected} := \overline{v_R} = v_{observed} \cdot k_{v_R}.$$

For example, in order to use the flow velocity $v_{observed}$ observed in the portion of the blood vessel to obtain the average flow velocity in the portion of the blood vessel over all positions of the free cross section Q of the flow channel of the blood vessel model $M_B^Q$, the average flow velocity $v_{average}$ in the fluid flow model $M_F^Q$ can be calculated as follows as reference flow velocity $v_{R\_average}$:

$$v_{average} := \frac{\int_Q M_F^Q(x) dx}{\int_Q dx}.$$

From the reference flow velocity $v_{R\_average}$, the associated relative fluid flow model $M_{Fr\_average}^Q$ can be calculated as follows:

$$M_{Fr\_average}^Q := \frac{M_F^D}{v_{average}}.$$

From the relative fluid flow model $M_{Fr\_average}^Q$ and the fluorescent light model $M_L^Q$, a correction factor $k_{average}$ can then be determined as follows:

$$k_{average} := \frac{1}{\int_Q M_{Fr\_average}^Q(x) \ M_L^Q(x) dx}.$$

The correction factor $k_{average}$ thus allows the flow velocity $v_{observed}$ observed in the portion of the blood vessel to be corrected as follows to a value to be expected in the fluid flow model $M_F^Q$ for the average flow velocity $\overline{v_{average}}$ in the blood vessel:

$$v_{corrected} = \overline{v_{average}} = v_{observed} \cdot k_{average}.$$

In the method, therefore, the fluid flow guided through the flow channel in the blood vessel model $M_B^Q$ is calculated by determining a correction factor $k\_v_R$ from the relative fluid flow model $M_{Fr}^Q$ to the reference flow velocity $v_R$ and the fluorescent light model $M_L^Q$, and by using the length L of the portion 901, 902, 903, ... of the blood vessel 88 and also the characteristic transit time τ for the fluorophore in the portion 901, 902, 903, ... of the blood vessel 88 to determine a fluorophore propagation speed which, by means of the correction factor $k\_v_R$, is corrected to a value corresponding to the reference flow velocity $v_R$. The correction factor $k\_v_R$ as the inverse of the expected value of the relative flow velocities in the relative fluid flow model $M_{Fr}^Q$, dependent on the spatial probability density described by the fluorescent light model $M_L^Q$ for the intensity of the remitted light at different positions over the free cross section Q of the flow channel in the blood vessel model $M_B^Q$, is determined according to the following rule:

$$k\_v_R = \frac{1}{\int_Q M_{Fr}^Q(x) M_L^Q(x) dx}.$$

The blood volume flow is preferably determined using a look-up table that contains pre-calculated correction factors for different fluid flow models $M_F^Q$ and/or different fluorescent light models $M_L^Q$. The associated correction factor can, for example, be pre-calculated according to the diameter D of the hollow cylinder of the blood vessel model $M_B^Q$ and stored as a tuple [diameter, k] in a table. This saves computing time and simplifies the method.

In order to determine the length, the mean diameter, a center line of the portion of the blood vessel as a parameter of the blood vessel model $M_B^Q$, and to determine the parameters of the fluid flow model $M_F^Q$ and/or the parameters of the fluorescent light model $M_L^Q$, it is advantageous to determine a selected image from the provided images using a criterion relating to the image brightness of the individual picture elements of the image, i.e. the intensity of the picture elements, as a measure of the intensity of the remitted light detected by the image acquisition device.

This criterion corresponds to a state in which the blood vessel in the image is maximally filled with the fluorescence agent. This measure increases the accuracy of the determination of the blood volume flow.

In order to determine the length of the portion of the blood vessel and/or the diameter of the portion of the blood vessel, a center line of the portion of the blood vessel is preferably determined in at least one of the provided images. The center line forms a central axis of the portion of the blood vessel, such that the distance to the blood vessel wall is the same at each location of the center line. The center line can be determined from a provided image by means of image processing. This ensures an automatic determination of the center line, so that no operator interaction, or as little operator interaction as possible, is necessary during the method for determining the blood volume flow, such that the method can be used in practice.

For this purpose, the portion of the blood vessel is firstly determined in a selected image using an image segmentation method. Here, a segmentation denotes an image which, for each pixel, specifies a class to which the pixel belongs. In particular, the segmentation is a binary image, where the value 1 means that the pixel belongs to the portion of the blood vessel and the value 0 means that the pixel does not belong to the portion of the blood vessel. In order to ensure a short computing time, adaptive thresholding methods in particular are suitable as segmentation methods, as described for example in the publication "Nobuyuki Otsu, A threshold selection method from gray-level histograms, IEEE Trans. Sys. Man. Cyber. 1979, vol. 9, no. 1, pp. 62-66", to which reference is hereby made in full and the disclosure of which is included in the description of this invention.

Other segmentation methods known to a person skilled in the art from the literature, in particular methods for segmenting blood vessels in medical images, can also be used instead of these methods. The surgeon can adapt the segmentation and/or select the portion of the blood vessel in which the blood volume flow is to be measured. The use of an image segmentation method has the advantage that the method can run as automatically as possible without any effort for the surgeon, and it is therefore suitable in practice for use during an operation.

In order to determine the center line from the segmentation of the portion of the blood vessel, pixels on the central axis of the portion of the blood vessel are preferably determined in a first step by processing the provided images, in particular the segmentation. To this end, it is possible to apply morphological operations such as the so-called erosion or so-called Voronoi diagrams or else other algorithms to the segmented images, for example a skeletonization algorithm as described in the article "Fixed Topology Skeletons, P. Gotland, W. Crimson, International Conference on Computer Vision and Pattern Recognition (CVPR), 2000", which is herewith referred to in its entirety and the disclosure of which is incorporated in the description of this invention.

A polygonal chain is then determined from the individual pixels on the central axis by connecting neighboring pixels. To increase the accuracy of the method, the length of the polygonal chain is minimized by adapting connection structures of the pixels along the central axis on the basis of their pixel neighborhoods. This reduces discretization errors. In particular, for each pixel along the center line, the pixel neighborhood surrounding it, for example the 8-pixel neighborhood, is taken into consideration. L-shaped connection structures between three consecutive pixels are replaced by diagonal connection structures in order to obtain a center line having a length that corresponds as far as possible to the length of the portion of the blood vessel. By fitting continuous functions, in particular Bezier splines, to the length-minimized polygonal chain, discretization errors can be further reduced and the accuracy of the method can thus be increased.

Preferably, the transit time is determined from the offset of a time development of the image brightness at at least two different sectors of the portion of the blood vessel by processing the provided images, with a continuous function being fitted to the time development of the image brightness at the different sectors of the portion of the blood vessel in each case. The transit time describes a time interval, characteristic of the fluorophore, for the propagation of the fluorophore in the portion of the blood vessel. To determine the transit time, a starting point and an end point on the center line of the portion of the blood vessel are determined between which the blood volume flow is to be ascertained.

In this case, the starting point lies in a range between 5% and 15%, preferably at 10%, of the overall length of the portion of the blood vessel, and the end point lies in a range between 80% and 95%, preferably at 90%, of the overall length of the portion of the blood vessel. This avoids inaccuracies when determining the center line, e.g., by the erosion of the segmentation, which occur especially at the start and end of a portion of a blood vessel, and the accuracy of the method is therefore increased. In this case, the starting point and the end point can be determined automatically on the basis of the center line and the specified ranges, or they can be set by a surgeon in the selected image. For the starting point and the end point, a sector is in each case determined which surrounds the respective point, e.g. a 5×5 neighborhood of pixels centered on the starting point or the end point. In order to determine the intensity profile, i.e. the profile of the image brightness at the respective point, the intensity in the sector is calculated in at least a plurality of the provided images by averaging the intensities over all the pixels of the sector. The averaging of the intensities over the entire sector increases the accuracy of the method. The intensity values at the starting point and at the end point are plotted over the different recording times of the images. A continuous function is fitted to these measured values in order to obtain a continuous time development of the image brightness at the respective point. In particular, a gamma function is used for this purpose. The time offset of the image brightness curves at the starting point and at the end point of the portion of the blood vessel represents the transit time.

The diameter of the flow channel cannot be determined directly from the segmentation of the portion of the blood vessel, since the segmentation does not distinguish between flow channel and blood vessel wall. Assuming a circular cross section of the blood vessel model $M_B^Q$, the total diameter of the cross section of the blood vessel model $M_B^Q$ can be determined on the basis of the segmentation. For this purpose, starting from points on the center line, a circle is determined in each case around the respective point, and its radius is increased until the edge of the circle coincides with the edge of the segmentation. The mean value of the diameters of the circles then corresponds to the diameter of the circular cross section of the blood vessel model $M_B^Q$. In order also to determine the diameter of the flow channel, it is necessary to differentiate between flow channel and blood vessel wall in the segmented portion in the provided images. In order to be able to make this differentiation with the greatest possible accuracy, it is advantageous if the width of the flow channel and the wall thickness of the blood vessel model $M_B^Q$ are determined using a criterion relating to the intensity profile orthogonal to the center line of the portion of the blood vessel in one or more of the provided images. In particular, it is advantageous that the criterion relating to the curve of the intensity profile takes into account the curvature of the curve of the intensity profile orthogonal to a center line of the portion of the blood vessel. One finding of the invention is in fact that points on the border between flow channel and blood vessel wall each correspond to a minimum of the curvature of the intensity profile orthogonal to the center line of the portion of the blood vessel. Using this criterion, a segmentation of the flow channel can then be determined from the segmentation of the portion of the blood vessel. The diameter of the flow channel can then be determined, as described above for the overall diameter, by increasing the diameter of circles on the center line of the portion of the blood vessel until the edge of the circle coincides with the flow channel edge.

From the transit time τ, the length L and the diameter D of the flow channel of the portion of the blood vessel and from the correction factor $k\_v_R$, the blood volume flow can then be calculated as $$I_{Bi} = \left(\frac{D}{2}\right)^2 \pi \frac{L}{\tau} k\_v_R.$$

Finally, it is also advantageous if, for the calculated blood volume flow in the portion of the blood vessel, a confidence interval based on the diameter and/or the length of the portion of the blood vessel and/or the transit time and/or a correction factor and/or the blood vessel model $M_B^Q$ and/or the fluid flow model $M_F^Q$ and/or the fluorescent light model $M_L^Q$ and/or the shape of a center line of the portion of the blood vessel is determined on the basis of error simulations. As a result, the accuracy of the blood volume flow determined using the method is quantified for the operator. This measure also contributes to the fact that the method can be used in practice.

In an advantageous development of the method, provision is made that, in order to determine the blood volume flow through a blood vessel in an operating region using a fluorophore, the blood vessel is divided into several portions, and the blood volume flow ($I_{Bi}$) in the portions is determined using an above-specified method for determining the blood volume flow in a portion of a blood vessel. The blood volume flow is determined with the proviso that, at a branch of the blood vessel, the sum of the blood volume flows ($I_{Bi}$) to the branch corresponds to the sum of the blood volume flows ($I_{Bi}$) from the branch. This method is based on the assumption that the volume of the blood is maintained over the course of the blood vessel. In order to ensure this, the determination of the blood volume flow in the individual portions of the blood vessel can be formulated as an optimization problem across all portions, in which the volume conservation at branches is included as a secondary condition. This has the advantage that the blood volume flow can be determined with greater accuracy by the simultaneous determination in a plurality of mutually dependent portions of the blood vessel.

The invention also extends to a computer program having a program code for carrying out the above-described method steps when the computer program is loaded on a computer unit and/or executed on a computer unit.

In addition, the invention extends to a surgical system for determining the blood volume flow ($I_{Bi}$) through a portion of a blood vessel in an operating region using a fluorophore. The surgical system contains an illumination device for providing fluorescence excitation light for the operating region, an image acquisition device for providing a plurality of images which are based on light having wavelengths within a fluorescence spectrum of the fluorophore and which show the portion of the blood vessel at different recording times, and a computer unit having a computer program with a program code for carrying out the above-described method steps for determining the blood volume flow.

Advantageous exemplary embodiments of the invention, which are schematically depicted in the drawings, are described below.

In the drawings:

FIG. 5A to FIG. 5F show a determination of a center line of a portion of a blood vessel;

FIG. 7A shows a blood vessel;

FIG. 7B shows a portion of the blood vessel;

FIG. 7C shows an intensity profile orthogonal to the center line of a portion of the blood vessel;

FIG. 7D shows flow channel edge points of a portion of a blood vessel;

FIG. 13A shows a horizontal cross section of a portion of a blood vessel with a first sector containing a starting point, and a second sector containing an end point;

FIG. 13B shows a vertical cross section of the portion of the blood vessel in FIG. 13A along the penetration depth x with the associated flow profile;

FIG. 13C shows a relative fluid flow model;

FIG. 13D shows a fluorescent light model;

FIG. 14A shows a horizontal cross section of a portion of a blood vessel with a first sector containing a starting point, and a second sector containing an end point;

FIG. 14B shows a time development of the intensity in a first sector and in a second sector of a portion of a blood vessel for determining a transit time;

Figure 1:
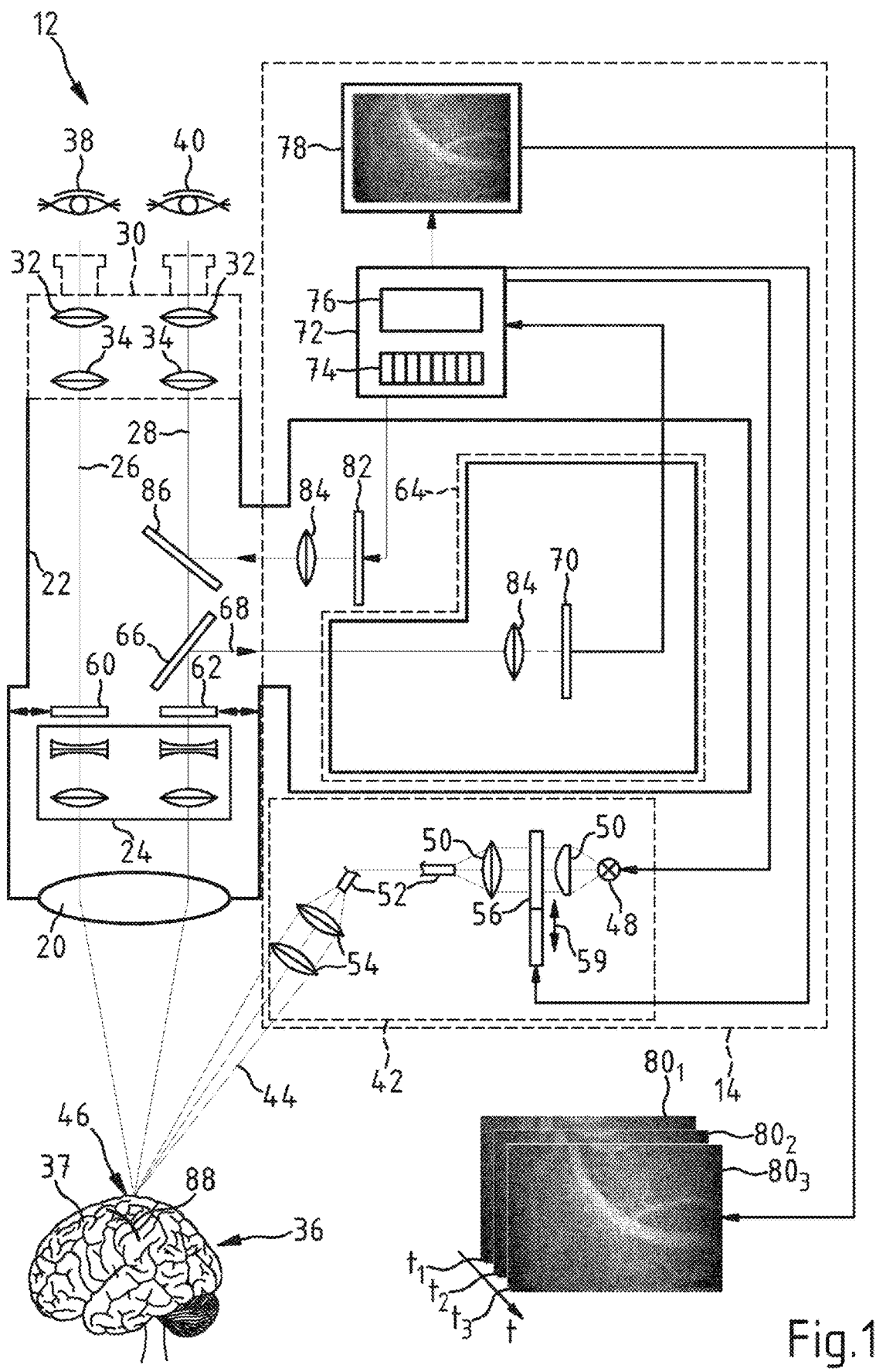
FIG. 1 shows a surgical microscope with a system for determining the blood volume flow through a portion of a blood vessel in an operating region.

The surgical microscope 12 shown in FIG. 1 contains a system 14 for determining the blood volume flow $I_{Bi}$ through a single portion of a blood vessel 88 in an operating region 36 and is designed for neurosurgical operations. The surgical microscope 12 has a microscope main objective 20. The microscope main objective 20 is received in a microscope main body 22. The microscope main body 22 contains an adjustable magnification system 24. A left and a right observation beam path 26, 28 passes through the microscope main objective 20. A binocular tube 30 is connected to a microscope main body 22. In the left and right observation beam path 26, 28, the binocular tube 30 contains an eyepiece lens 32 and a tube lens 34. By way of the binocular tube 30, an observer is able, in the present case, to stereoscopically observe an operating region 36 at a brain 37 of a patient, using a left and a right observer eye 38, 40.

In the system 14 for determining the blood volume flow $I_{Bi}$ there is an illumination device 42. By way of an illumination beam path 44, the illumination device 42 provides illumination light 46 for the operating region 36. The illumination device 42 comprises a xenon light source 48. The illumination device 42 contains further optical elements in the form of lenses 50, a light guide 52 and an illumination objective 54. The light of the xenon light source 48 is coupled into a light guide 52 by a lens system containing lenses 50. From the light guide 52, illumination light 46 reaches the operating region 36 through an illumination objective 54.

The illumination device 42 contains a switchable filter assembly for adjusting the spectral composition of the illumination light 46. This filter assembly contains an illumination filter 56. In accordance with the arrow 59, the illumination filter 56 can be moved into the illumination beam path 44 and can be moved out of the illumination beam path 44.

The illumination filter 56 is a bandpass filter. It is permeable to light from the xenon light source 48 in the spectral range between 780 nm and 810 nm. By contrast, light in the spectral range below 780 nm and above 810 nm is filtered or significantly suppressed by the illumination filter 56.

An observation filter 60 for the left observation beam path 26 and an observation filter 62 for the right observation beam path 28 are situated in the microscope main body 22 on the side of the magnification system 24 distant from the microscope main objective 20. In accordance with the double-headed arrows, the observation filters 60, 62 can be moved into or out of the observation beam path 26, 28. The illumination filter 56 and the observation filters 60, 62 have filter characteristics matched to one another. To observe the operating region 36 with fluorescent light, the illumination filter 56 is inserted into the illumination beam path 44, and the observation filters 60, 62 are arranged in the observation beam paths 26, 28.

The system 14 for determining the blood volume flow $I_{Bi}$ in the surgical microscope 12 has an image acquisition device 64, which is used for acquiring images $80_1$, $80_2$, $80_3$, $80_4$, of the operating region 36. Observation light from the operating region 36 can be supplied to the image acquisition device 64 from the right observation beam path 28, which has an optical axis 68, through the observation filter 62 and via an output coupling beam splitter 66. There is an image sensor 70 in the image acquisition device 64. The image sensor 70 is sensitive to the emission wavelength of the fluorophore ICG, which is in the spectral range from 810 nm to 830 nm, said fluorophore being fed into the bloodstream of a patient in order to determine the blood volume flow $I_{Bi}$ in a blood vessel.

The image sensor 70 of the image acquisition device 64 is connected to a computer unit 72. The computer unit 72 comprises an input unit 74 and contains a program memory 76. The computer unit 72 is connected to a screen 78. Images $80_1$, $80_2$, $80_3$, $80_4$, . . . of the operating region 36 captured at different recording times $t_1$, $t_2$, $t_3$, $t_4$, . . . are displayed on the screen. The computer unit 72 controls a display 82. By way of a beam splitter 86, the display on the display 82 is overlaid on the observation light in the right observation beam path 28 via a lens 84. For an observer, the display on the display 82 is thus visible simultaneously with the operating region 36 in the right eyepiece of the binocular tube 30.

Figure 2:
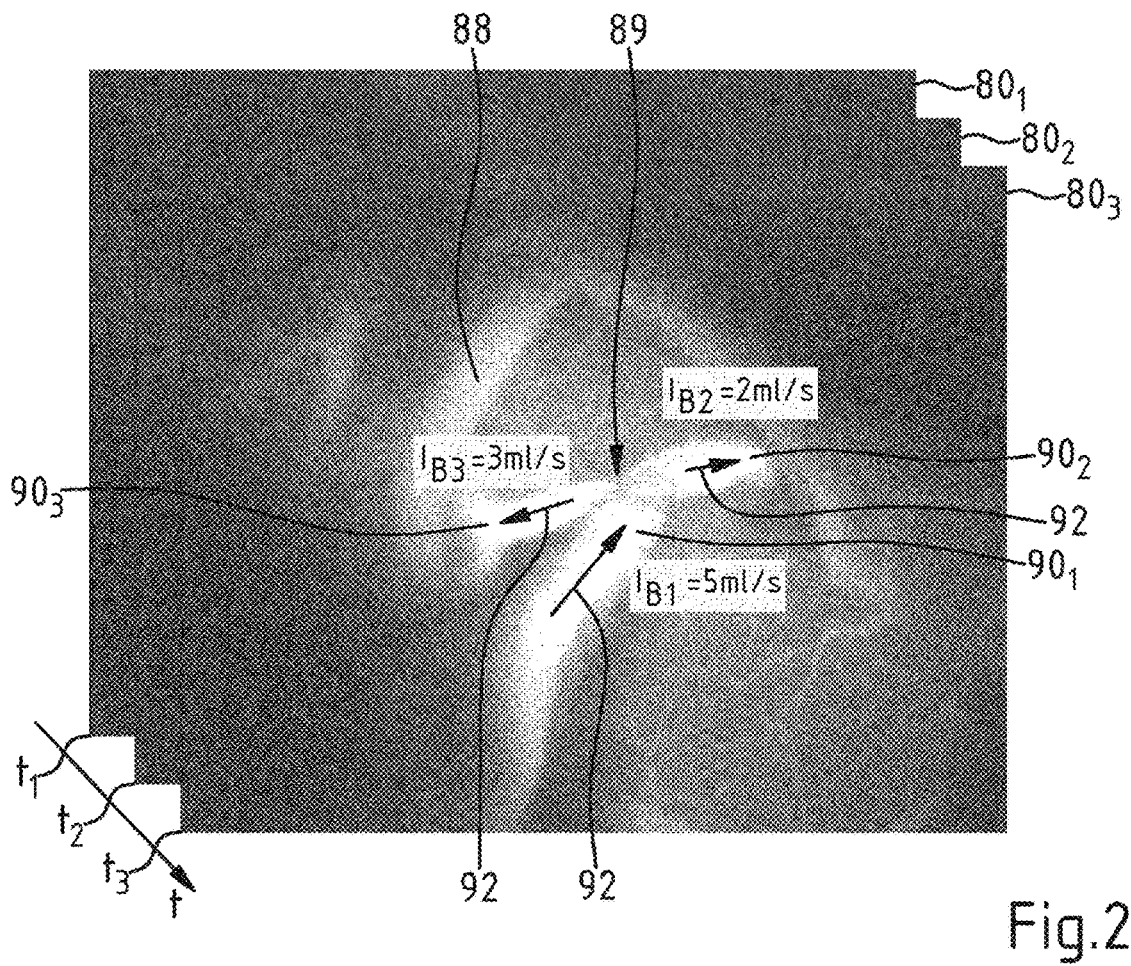
FIG. 2 shows several images of the operating region with a blood vessel.

FIG. 2 shows several images $80_1$, $80_2$, $80_3$, . . . of the surgical region 36, which were acquired at different recording times $t_1$, $t_2$, $t_3$, . . . by means of the image acquisition device 64. The images $80_1$, $80_2$, $80_3$, . . . each contain a blood vessel 88 which has three spatially separated portions $90_i$, i=1, 2, 3. In the images $80_1$, $80_2$, $80_3$, . . . , a blood volume flow $I_{Bi}$ is identified by the arrows 92. The direction of the arrows 92 corresponds to the direction of the blood volume flow $I_{Bi}$, and the length of the arrows 92 corresponds to the amount of the blood volume flow $I_{Bi}$ in the respective portions $90_i$ of the blood vessel 88.

The blood volume flow $I_B$ in the entire blood vessel 88 consists of the blood volume flows $I_{BI}$ in individual portions $90_i$, i=1, 2, 3 of the blood vessel 88. At the branch 89 visible in FIG. 2 and having the blood vessel 88, the blood volume flow $I_{B1}$ of the blood flowing to the branch 89 is $I_{B1}$=5 ml/s. The blood volume flow $I_{B2}$ and $I_{B3}$ in the portions $90_2$, $90_3$ after the branch 89 are $I_{B2}$=2 ml/s and $I_{B3}$=3 ml/s. Hence, $I_{B1}=I_{B2}+I_{B3}$, i.e. the sum of the blood volume flows $I_{B2}$, $I_{B3}$ after the branch 89 corresponds to the blood volume flow $I_{B1}$ before the branch 89. This relationship means that the blood volume is maintained at a branch 89 in the blood vessel system.

The condition that the blood volume is maintained at a branch 89 in the blood vessel system can be used as a linear constraint for an optimization problem which, over all the portions $90_i$, i=1, 2, 3, . . . of a blood vessel 88 at the same time, defines the blood volume flow $I_{BI}$ based on the respective data at the portion $90_i$.

A computer program is loaded into the program memory 76 of the computer unit 72 and is used to determine the blood volume flow $I_{Bi}$ through a portion $90_i$ of a blood vessel 88 in the operating region 36 using a fluorophore.

The computer program contains a blood vessel model $M_B^Q$, which describes the geometry of a portion $90_i$ of the blood vessel 88.

Figure 3:
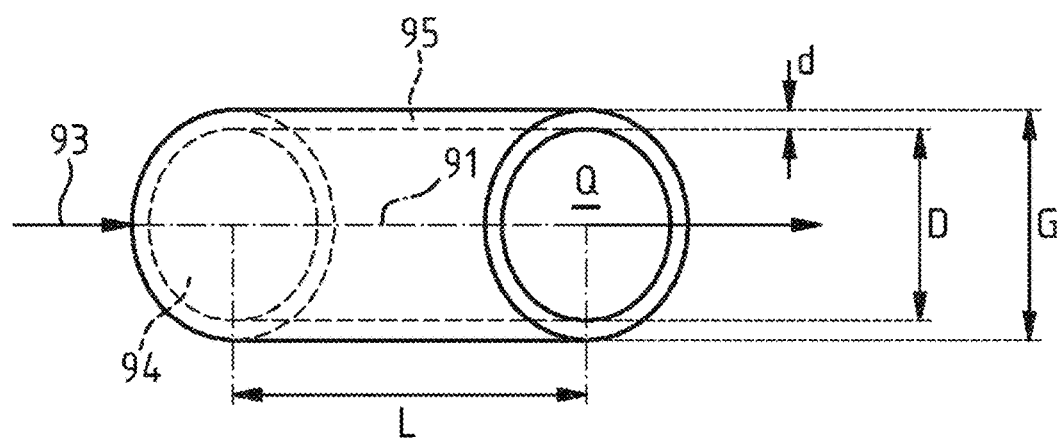
FIG. 3 shows a blood vessel model.

FIG. 3 shows a blood vessel model $M_B^Q$, which describes a portion $90_i$, i=1, 2, 3 of the blood vessel 88 shown in FIG. 2, through which the blood of a patient flows, as a hollow cylinder of length L and cylinder axis 91, which has a wall 95 with wall thickness d and which forms a flow channel 94 delimited by the wall 95 of the hollow cylinder, the flow channel 94 having a circular cross section Q, an inside diameter D and an outside diameter G and allowing fluid to flow through it in the direction of the arrows 93.

The parameters of the blood vessel model $M_B^Q$ are determined in the computer program, which is loaded into the program memory 76 of the computer unit 72, by processing at least one of the provided images $80_1$, $80_2$, $80_3$, $80_4$, . . . of the portion $90_i$ of the blood vessel 88. For this purpose, a selected image is determined from the plurality of images $80_1$, $80_2$, $80_3$, $80_4$, . . . on the basis of a criterion relating to the image brightness of the picture elements of the image, i.e. the intensity of the picture elements. Since the fluorescent light causes a particularly high intensity of picture elements in the images, the state in which the blood vessel is maximally filled in the image with the fluorescence agent is determined by the following criterion:

$$I_{max}:=\max\{I(x)|x\in\Omega\}$$

$$A:=I_{max}\cdot|\{x\in\Omega|I(x)=I_{max}\}|,$$

where Ω denotes the set of picture elements x in an image and I(x) denotes the image brightness of the image at this picture element, referred to as the intensity of the picture element x in the present case.

Maximizing the value A ascertains the image which has a high maximum intensity $I_{max}$ and, at the same time, a large number of pixels which assume this maximum intensity value.

Figure 4A:
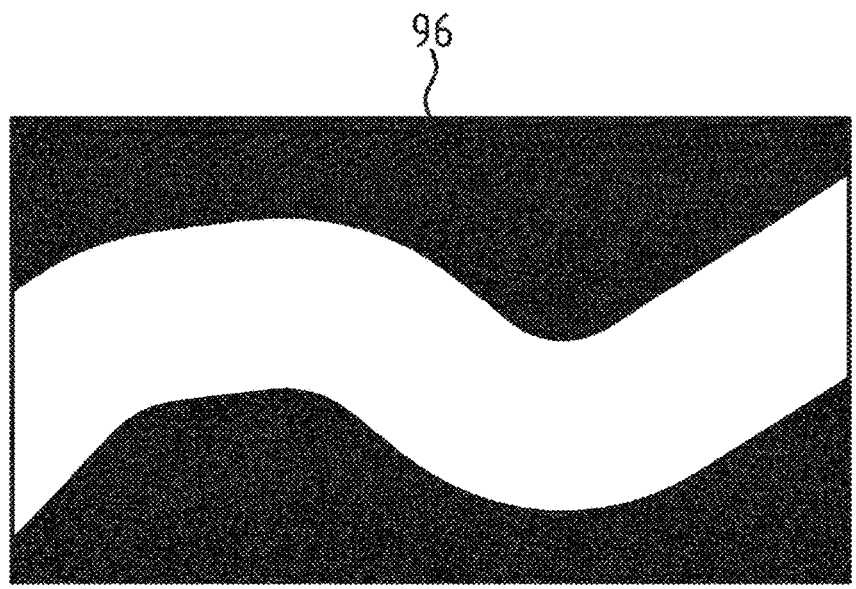
FIG. 4A shows a segmentation of a portion of a blood vessel.

For the portion $90_i$ of the blood vessel 88, as shown in FIG. 4A, a segmentation 96 and a starting point $P_1$ and an end point $P_2$ of the portion $90_i$ of the blood vessel 88 are then determined. The segmentation 96 is determined using Otsu thresholding as described in the publication "*A threshold selection method from gray-level histograms*, Nobuyuki Otsu, IEEE Trans. Sys. Man. Cyber. vol. 9, no. 1, pp. 882-886, 1979", to which reference is hereby made in its entirety and the disclosure of which is included in the description of this invention. This initial segmentation 96 is improved using a gradient-based segmentation method explained with reference to FIGS. 7A to 7F.

Figure 4B:
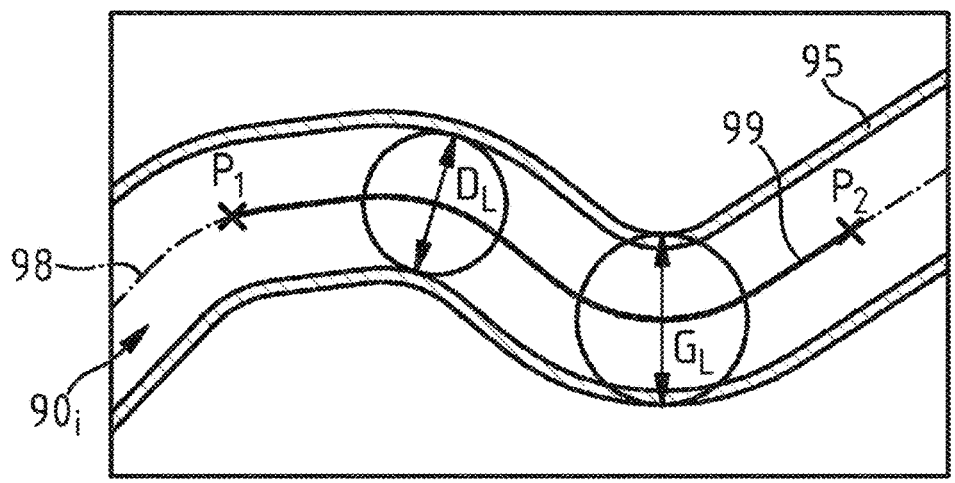
FIG. 4B shows a horizontal cross section of a blood vessel model with parameters of the blood vessel model.

For the segmentation of a portion $90_i$ of the blood vessel 88 as shown in FIG. 4A, FIG. 4B shows a horizontal cross section of a blood vessel model $M_B^Q$ with its parameters which, in the computer program for determining the blood volume flow $I_{Bi}$ through the portion $90_i$ of the blood vessel 88 in the operating region 36 using a fluorophore, are determined from the segmentation 96. In this case, the center line 98 is ascertained by means of erosion from the segmentation 96 of the portion $90_i$ of the blood vessel 88. A starting point $P_1$ and an end point $P_2$ of the portion $90_i$ of the blood vessel 88 are defined between which the blood volume flow $I_{Bi}$ is determined. In this case, the starting point $P_1$ and the end point $P_2$ are located on the center line 98. Moreover, the starting point $P_1$ lies in a range between 5% and 15%, preferably at 10%, of the overall extent of the portion $90_i$ of the blood vessel 88 along the length, and the end point $P_2$ lies in a range between 80% and 95%, preferably at 90%, of the overall extent of the portion $90_i$ of the blood vessel along the length. This avoids inaccuracies when determining the center line 98, which inaccuracies occur in particular at the start and at the end of a portion $90_i$ of a blood vessel 88.

The starting point $P_1$ and the end point $P_2$ can be determined automatically by means of image processing on the basis of the center line 98 and the specified ranges, or they can be set by a surgeon in the selected image. The length L of the portion $90_i$, considered for blood volume flow determination, of the blood vessel 88 is determined by ascertaining the length of the center line portion 99 of the center line 98 between the starting point $P_1$ and the end point $P_2$. To determine an overall diameter G of the portion $90_i$ of the blood vessel 88, a local overall diameter $G_L$ is determined at any point along the center line 98 between the starting point $P_1$ and the end point $P_2$, by defining a circle around each point and increasing its radius until the edge of the circle touches the edge of the blood vessel 88. The edge of the blood vessel 88 can be ascertained, as in FIG. 4A, by determining the edge of the segmentation 96 of the blood vessel 88. The overall diameter G of the blood vessel 88 then corresponds to the mean value of all the local overall diameters $G_L$.

To determine a diameter D of the flow channel 94 of the portion 90 of the blood vessel 88, a local diameter $D_L$ is determined at each point along the center line 98 between the starting point $P_1$ and the end point $P_2$, by defining a circle around each point and increasing its radius until the edge of the circle touches the inside of the wall 95 of the blood vessel 88. The inside of the wall 95 of the blood vessel 88 can be ascertained by determining the edge of the segmentation 96 of the flow channel as in FIGS. 7A to 7D. The diameter D of the flow channel 94 then corresponds to the mean value of all the local diameters $D_L$.

FIGS. 5A to 5F explain a determination of a center line 98 of the portion 90 of the blood vessel 88 and a determination of the length L of the portion 90 of the blood vessel 88, considered for determining the blood volume flow, between the starting point $P_1$ and the end point $P_2$ in the computer program. FIG. 5A shows a portion 90 of the blood vessel 88 with the center line 98. In the image acquisition device 64, the portion 90 of the blood vessel 88 is imaged onto a region 71 of the image sensor 70 of the image acquisition device 64 shown in FIG. 5B, with a resolution evident from FIG. 5C. FIG. 5D shows the pixels belonging to the discretized center line 102 on the image sensor 70, and FIG. 5E shows the polygonal chain 104 of the discretized center line 102. The computer program contains a post-processing routine that post-processes this polygonal chain 104, as can be seen in FIG. 6, in order as far as possible to avoid discretization errors when determining the length of the center line 98 between the starting point $P_1$ and the end point $P_2$. These discretization errors, resulting from experiments, are 6.3% on average, as described in the article "A. Naber, D. Berwanger, W. Nahm, In Silico Modelling of Blood Vessel Segmentations for Estimation of Discretization Error in Spatial Measurement and its Impact on Quantitative Fluorescence Angiography, 41st Annual International Conference of the IEEE Engineering in Medicine and Biology Society (EMBC), 2019". As is shown in FIG. 5F, continuous functions 106 in the form of splines are fitted to the post-processed polygonal chain 104, and the length L of the center line portion 99 of the portion 90 of the blood vessel 88 between the starting point $P_1$ and the end point $P_2$ is calculated using an arc integral in order to further reduce the discretization error.

Figure 6A:
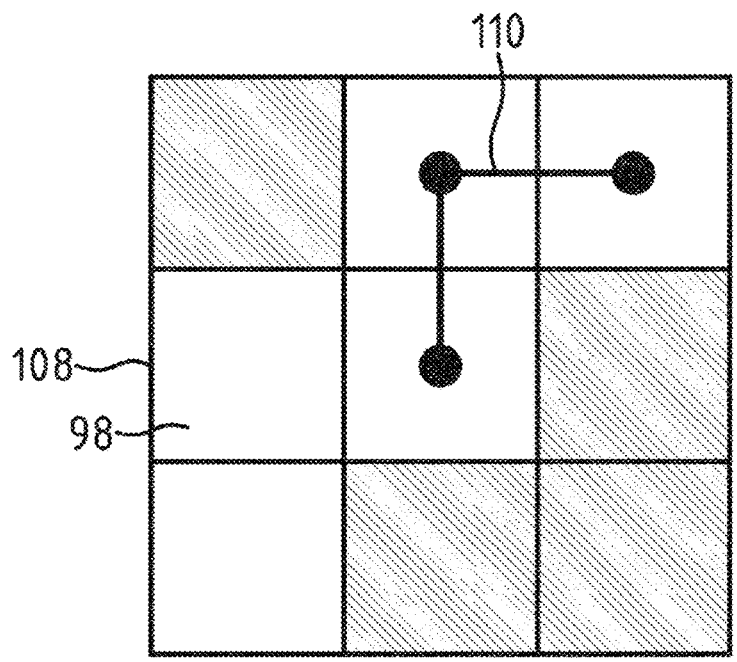
FIG. 6A shows a detail of a polygonal chain shown in FIG. 5E.
Figure 6B:
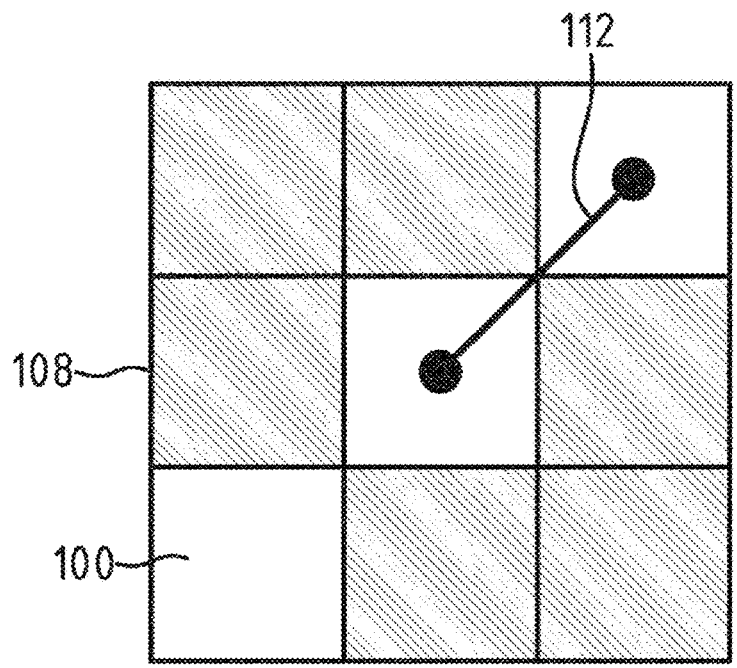
FIG. 6B shows post-processing of the detail of the polygonal chain shown in FIG. 6A.

As is shown in FIGS. 6A and 6B, the post-processing routine of the computer program corrects the center line 98 of the polygonal chain 104, shown in FIG. 5E, of the center line 98 by taking account of pixel neighborhoods in order to reduce discretization errors. For this purpose, the pixel neighborhood 108 surrounding each pixel, here the 8-pixel neighborhood 108, is considered for each pixel along the center line 98. L-shaped connection structures 110 as in FIG. 6A are thereby replaced by diagonal connection structures 112 in FIG. 6B. In this way, the length of the center line 98 is minimized, and a post-processed center line 100 results. As an alternative to the 8-neighborhood, other pixel neighborhoods can also be considered.

FIGS. 7A to 7D explain the determination of the diameter D of the flow channel 94 and the wall thickness d of the blood vessel model $M_B^Q$ in the computer program on the basis of one of the images $80_1$, $80_2$, $80_3$, $80_4$, . . . acquired by the image acquisition device 64 and thus made available. Since a wall 95 of the blood vessel scatters a fluorescence signal, the boundary between the flow channel 94 and the wall 95 of the blood vessel is not uniquely identifiable in an image acquired by means of the image acquisition device 64. FIG. 7A shows a blood vessel 88 with a portion $97_i$, selected therein, of one of the images $80_1$, $80_2$, $80_3$, $80_4$, . . . . The selected portion $91_i$ of the blood vessel 88 can be seen in FIG. 7B. A local intensity profile I(x) in the selected image is shown in FIG. 7C as a curve 114 along the distance x orthogonal to the center line 98 of the portion $90_i$ of the blood vessel 88. The portion $90_i$ of the blood vessel 88 is described by the blood vessel model $M_B^Q$ as a flow channel 94 with a circular cross section, which has the diameter D and is delimited by a wall 95 with the wall thickness d. The diameter D of the flow channel 94 and the wall thickness d of the blood vessel model $M_B^Q$ are determined on the basis of a criterion relating to the intensity profile I(x) orthogonal to the center line 98 of the portion 90$_i$ of the blood vessel 88 in one or more of the provided images 80$_1$, 80$_2$, 80$_3$, 80$_4$, . . . .

The criterion relating to the intensity profile I(x) for determining the diameter D and the wall thickness d of the blood vessel model $M_B^Q$ can be, for example, the curvature of the intensity profile I(x) orthogonal to the center line 98 of the flow channel 94, a boundary between flow channel 94 and wall 95 being defined at the so-called flow channel edge points 116, where the curvature in the form of the second derivation of the intensity profile I(x) reaches a minimum, as viewed outward from the center line 98, and the intensity I(x) assumes the intensity value 115.

The motivation for this criterion is that the inventors used a surgical microscope 12 to record images of a material with a known wall thickness, in this case a silicone tube filled with a blood-like medium and ICG dye, and examined the intensity profile I(x) orthogonal to the center line 98 of the silicone tube in the acquired images 80$_1$, 80$_2$, 80$_3$, 80$_4$, . . . . This was repeated for different diameters of the silicone tube and for different arrangements of the latter under the surgical microscope 12. The inventors have found that the curvature of the intensity profile I(x) orthogonal to the center line of the silicone tube in the acquired images 80$_1$, 80$_2$, 80$_3$, 80$_4$, . . . is in particular suitable as a criterion for determining the diameter D of the flow channel 94. The curvature of the intensity profile I(x) is determined in the form of the second derivation of the intensity profile I(x). In this procedure, the boundary between flow channel 94 and wall 95 corresponds to those points at which the curvature of the intensity profile I(x) reaches a minimum, as viewed outward from the center line 98.

In order to determine the boundary between flow channel 94 and wall 95, the computer program therefore determines, in each case for points on the center line 98 of the portion 90$_i$ of the blood vessel 88, the flow channel edge points 116 as the first two points 115 where the curvature of the intensity profile I(x) in the form of the second derivation orthogonal to the center line 98 has a minimum. The local diameter $D_L$ at the respective point on the center line 98 is determined from the distances between these two flow channel edge points 116. By averaging the local diameters $D_L$ for all points on the center line 98, the diameter D of the flow channel 94 is determined. The distance between a flow channel edge point 116 and the edge of the segmented portion 90 of the blood vessel 88 then corresponds to the local wall thickness $d_L$. This is likewise averaged for all points along the center line 98, and the wall thickness d of the portion 90 of the blood vessel 88 is determined therefrom. A segmentation 96 of the flow channel 94 is determined by connecting the flow channel edge points 116.

The computer program for determining the blood volume flow $I_{Bi}$ through a portion i of a blood vessel 88 in the operating region 36 by means of a fluorophore contains, in addition to the blood vessel model $M_B^Q$, a fluid flow model $M_F^Q$ which describes a local flow velocity 122 at different positions over the free cross section Q of the flow channel 94 in the blood vessel model $M_B^Q$.

Figure 8:
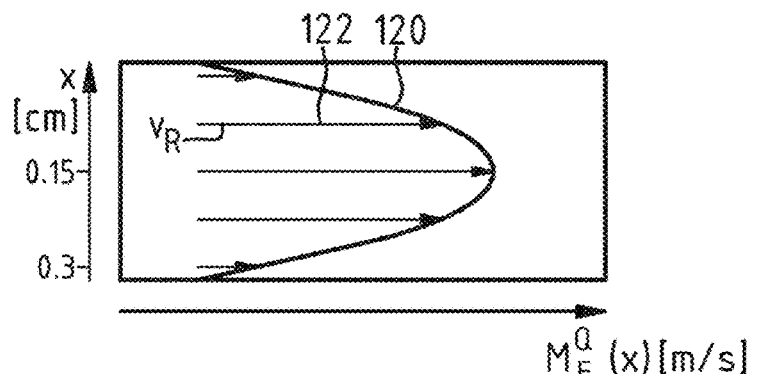
FIG. 8 shows a fluid flow model with an absolute flow profile.

FIG. 8 shows a flow profile 120 with different local flow velocities 122 along the diameter D of the cross section Q of the flow channel 94 of the blood vessel model $M_B^Q$ from FIG. 3. The fluid flow model $M_F^Q$ of the computer program here describes the flow profile 120 of a laminar fluid flow through the flow channel 94 of the blood vessel model $M_B^Q$. It is defined on a chord of the cross section Q of the flow channel 94, namely along the diameter D, and has the following mapping rule:

$$M_F^Q: [0,D] \rightarrow \mathbb{R}.$$

Figure 9A:
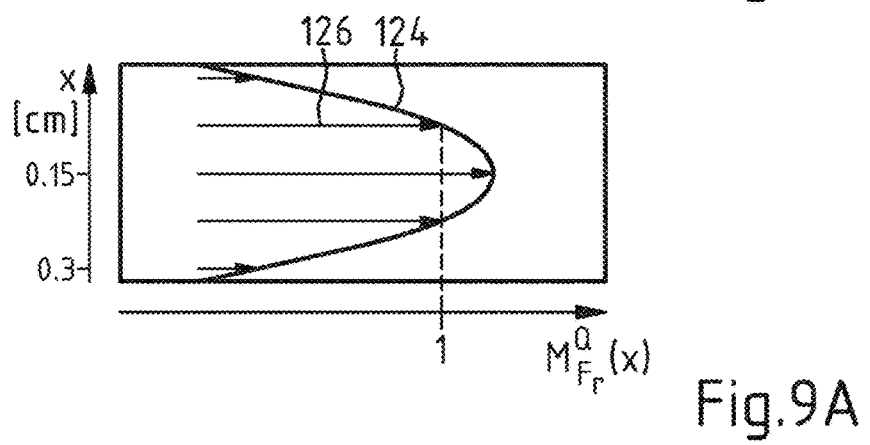
FIG. 9A shows a relative fluid flow model.
Figure 9B:
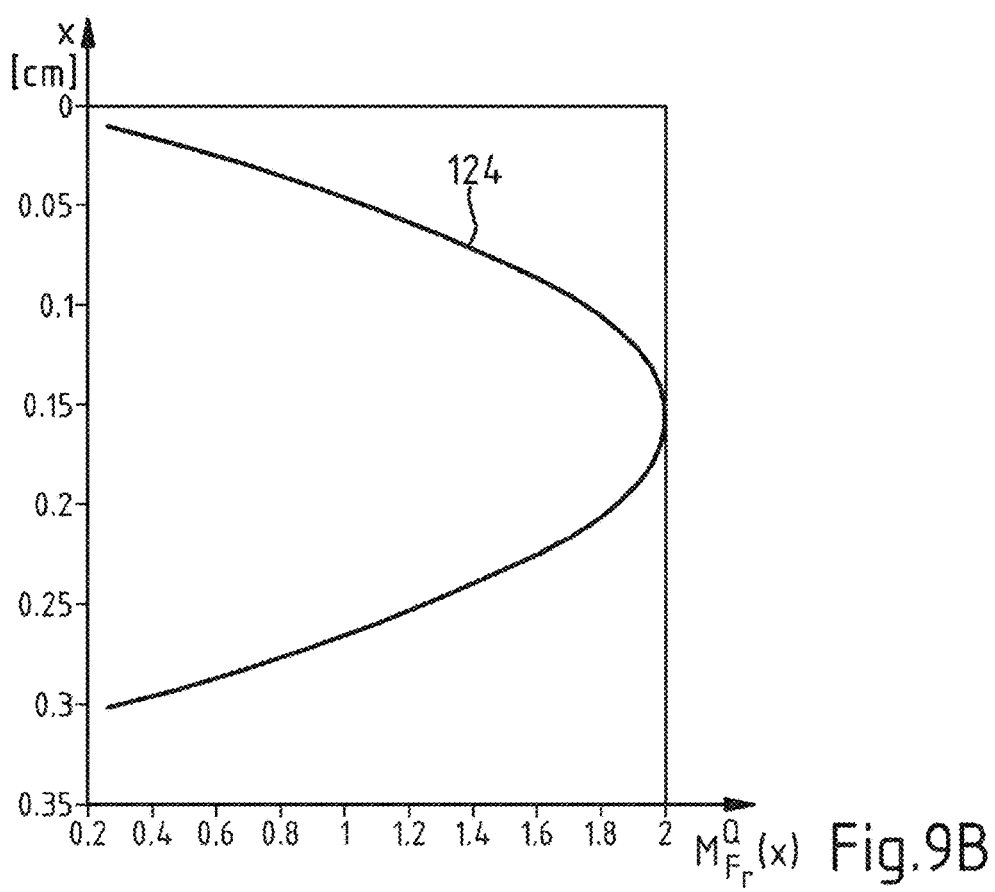
FIG. 9B shows a relative fluid flow model with a relative flow profile in the form of a parabola to a blood vessel with a diameter of 3 mm.

The fluid flow model $M_F^Q$ thus assigns the local flow velocity 122 to each position along the diameter D of the cross section Q of the flow channel 94. FIG. 9A and FIG. 9B each show a relative fluid flow model $M_{Fr}^Q$, which indicates a relative flow profile 124 of a laminar fluid flow through the flow channel 94 of the blood vessel model $M_B^Q$.

It describes a local relative flow velocity 126 at different positions across the diameter D of the cross section Q of the flow channel 94 in the blood vessel model $M_B^Q$ in FIG. 3 in relation to a reference flow velocity $v_R$. The reference flow velocity $v_R$ is determined from the local flow velocities 122 indicated in FIG. 8, in particular by selecting a specific flow velocity in the flow profile 124 as shown in FIG. 9A or by averaging all of the local flow velocities 122 in the flow profile 120 as seen in FIG. 9B. In order to specify a relative fluid flow model $M_{Fr}^Q$, with a relative flow profile 124, the values of the flow profile 120 in FIG. 8 are divided by the value of the reference flow velocity $v_R$. The fluid flow model $M_F^Q$ shown in FIG. 9B in the form of a relative fluid flow model $M_{Fr}^Q$, describes a laminar flow to a diameter D of 3 mm with a relative flow profile 124 to a reference flow velocity $v_R$ in the form of the mean value over all the local flow velocities 122. The relative flow profile 124 here has the shape of a parabola $$M_F^Q(x) = a(x-b)^2 + c$$

where $$a = \frac{-8}{D^2}, \quad b = \frac{D}{2}, \quad c = 2.$$

Figure 10:
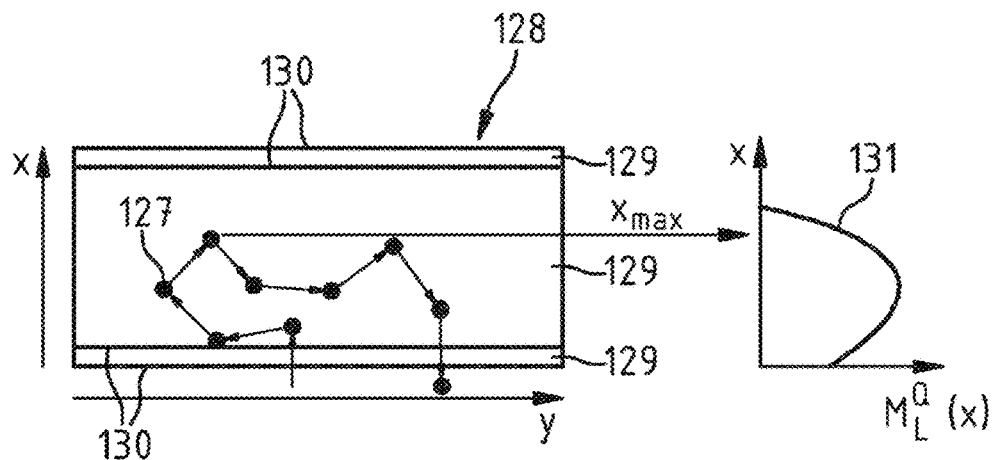
FIG. 10 shows a simulation for the propagation of photons in a blood vessel model for determining a fluorescent light model.

The computer program for determining the blood volume flow $I_{Bi}$ through a portion i of a blood vessel 88 in the operating region 36 by means of a fluorophore also contains a fluorescent light model $M_L^Q: Q \rightarrow \mathbb{R}$, which describes a spatial probability density for the intensity of the remitted light at different positions over the free cross section Q of the flow channel 94 in the blood vessel model $M_B^Q$, which light is emitted by a fluid which is mixed with fluorophore and flows through the free cross section Q of the flow channel 94 in the blood vessel model $M_B^Q$ when said fluid is irradiated with fluorescence excitation light. The fluorescent light model $M_L^Q$ is determined using a Monte Carlo simulation for the propagation of photons 127 in the blood vessel model $M_B^Q$, as shown in FIG. 10 and indicated in the abovementioned publication by L. Wang and S. Jacques. The blood vessel model $M_B^Q$ is assumed to be a layer model 128 with three layers: blood vessel wall—flow channel—blood vessel wall. The layer model 128 is irradiated with light, and the path of the photons 127 within the layer model 128 is followed. The photons 127 are assumed to be particles scattered at scattering centers, and the scattering centers in the flow channel 94 and in the wall 95 of the blood vessel model $M_B^Q$ each have a characteristic scattering center distribution. When hitting a scattering center, the photons 127 are scattered with a certain probability and are absorbed with another probability. In order to determine the fluorescence light model $M_L^Q$, a determination is carried out, for each remitted photon 127 that again leaves the layer model 128 through the same layer through which it entered the layer model 128, to ascertain the maximum penetration depth $x_{max}$ that this photon 127 has reached in the layer model 128. The different penetration depths of the photons 127 into the layer model 128 correspond to the diameter D of the cross section Q of the flow channel 94. In the implementation, it is advantageous to divide the diameter D into n equal sections, e.g. for n=100.

The graph 131 in FIG. 10 shows, for different penetration depths x along the diameter D, the proportion of the photons 127 which are remitted from the layer model 128 and whose maximum penetration depth $x_{max}$ corresponds to the value x. Since the fluorescent light model $M_L^Q$ represents a probability density, the following applies:

$$\int_Q M_L^Q(x)dx = 1.$$

This probability density is at the same time a measure of the intensity of the remitted light at different positions over the free cross section Q of the flow channel 94 in the blood vessel model $M_B^Q$, since the probability of a photon 127 reaching a certain penetration depth is also a measure of the intensity of the light remitted from this depth.

Figure 11:
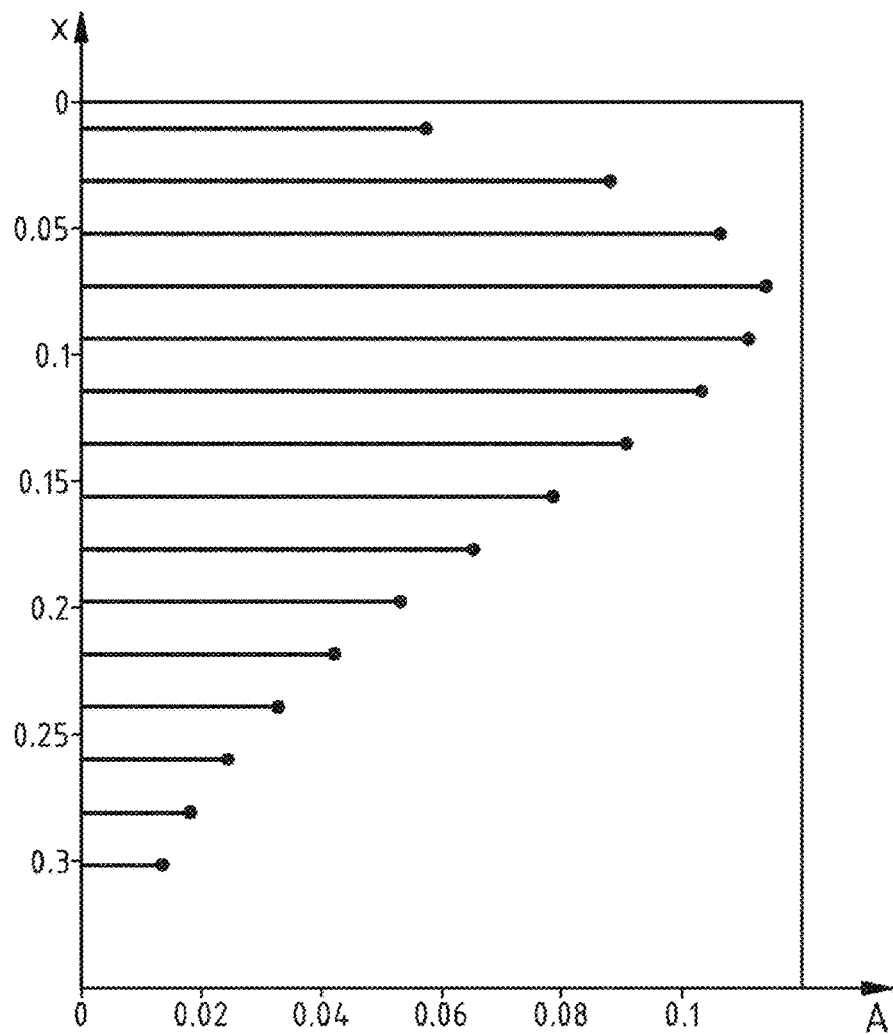
FIG. 11 shows a fluorescent light model determined using a simulation.

FIG. 11 shows a fluorescent light model $M_L^Q$. determined using a Monte Carlo simulation as described above. The penetration depth x along the diameter D of the flow channel is plotted on the vertical axis. The proportion A of the photons 127 shown in FIG. 10 which have reached the maximum penetration depth x during the simulation, and which have exited through the same wall 95 of the blood vessel model $M_B^Q$ through which they entered the model, is plotted on the horizontal axis.

Figure 12:
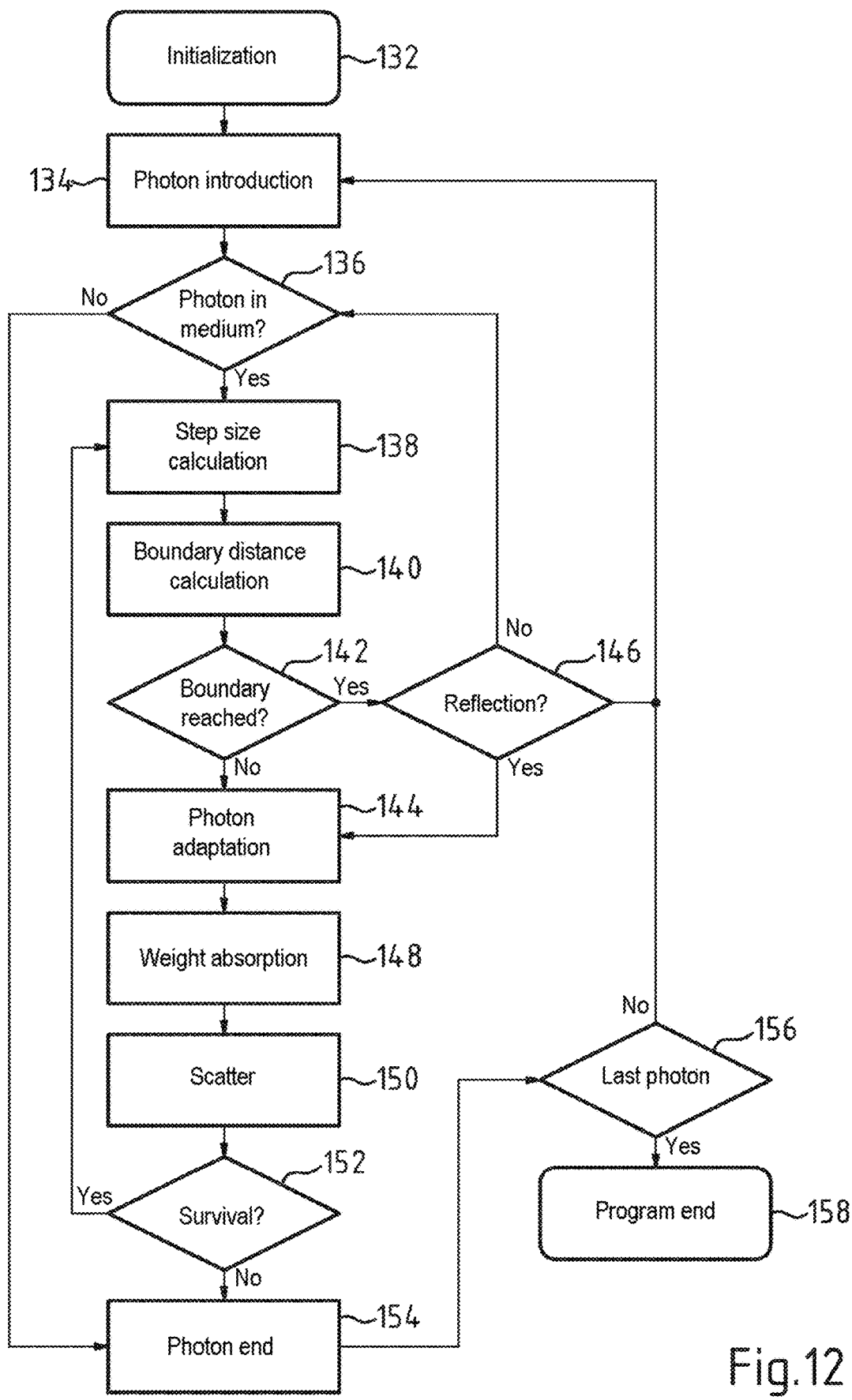
FIG. 12 shows a flow chart of a simulation algorithm for the propagation of photons in a blood vessel model.

FIG. 12 shows a flow chart for the simulation of photon motion in the layer model 128 as described in the above-mentioned publication by Wang and Jacques. In an initialization step 132, the program is initialized and the parameters are loaded. Thereafter, in a step of photon introduction 134, the simulation of a photon 127 with a fixed initial weight is started. In a query 136, a check is made as to whether the photon 127 has entered the layer model 128 or whether it has already been reflected by specular reflection before entering the layer model 128. If the photon 127 has entered the layer model 128 and is located in a layer 129, a step size calculation 138 is effected to determine a step size of the photon, depending on the properties of the medium in this layer 129, using a probability distribution over the free path length of the photon 127. In a step of boundary distance determination 140, the distance to the layer boundary 130 of the next layer 129 in the direction of motion of the photon 127 is determined. In a subsequent query 142, a check is made as to whether the photon 127 would reach or exceed a layer boundary 130 of the layer 129 in its direction of movement in the next step with the determined step size. If this is not the case, the location of the photon 127 is adapted in a photon adaptation step 144 using its step size. However, if the photon 127 reaches or exceeds a layer boundary 130, a query 146 is made to check whether the photon 127 is reflected at this layer boundary 130 or is transmitted to the next layer 129. If the photon 127 is transmitted to the next layer 129, parameters of the photon 127, e.g. the step size, are adapted to the next layer 129, and the steps described above are repeated, starting from the query 136 as to whether the photon 127 is in the medium. If the photon 127 is reflected at the layer boundary 130 of the layer 129, the location and the direction of the photon are adapted in the photon adaptation step 144 on the basis of the parameters of the photon 127. In a step of weight absorption 148, the weight of the photon 127 is reduced on account of absorption by the interaction site. A part of the current weight of the photon 127 is deposited at the local site of the layer model 128, and the weight of the photon 127 is adapted. After the movement of the photon 127 and the reduction in the weight, the photon 127 is scattered in a step of scattering calculation 150 based on the properties of the medium and various statistically determined angles, and its parameters are adapted. In order to terminate photons 127 of very low weight, whose further movement have only very small effects on the model, a query 152 uses a random value to check whether the photon 127 survives further in the simulation or whether it is to be terminated in a photon end 154 step. If it is the last photon 156 in the simulation, then, in a last step of the program end 158, the program is terminated. Otherwise, in the step of photon introduction 134, the next photon 127 is introduced into the layer model 128.

In order to determine the fluorescent light model $M_L^Q$ on the basis of this simulation, the inventors have determined the movement of 1,000,000 photons 127 using the following parameters for a layer model 128 with three layers 129:

|  | blood vessel wall | flow channel |
|---|---|---|
| absorption coefficient $\mu_a$ | 2.25 cm$^{-1}$ | 7.38 cm$^{-1}$ |
| scattering coefficient $\mu_s$ | 200 cm$^{-1}$ | 713 cm$^{-1}$ |
| refractive index n | 1.44 | 1.38 |
| anisotropy g | 0.99 | 0.99 |

FIG. 13A shows a horizontal cross section of a portion $90_i$ of a blood vessel 88 with a starting point $P_1$ and an end point $P_2$ on the center line 98 of the portion $90_i$ of the blood vessel 88, and also a first sector $A_1$, which contains the starting point $P_1$, and a second sector $A_2$, which contains the end point $P_2$.

FIG. 13B shows, for the first sector $A_1$ in FIG. 13A, a vertical cross section of the portion $90_i$ of the blood vessel 88 along the penetration depth $x \in D$. For each penetration depth x, the associated local relative flow velocity 126 is indicated by the relative fluid flow model $M_{Fr}^Q$ in FIG. 13C, and the proportion of photons 127 that are remitted from the respective penetration depth x are indicated by the fluorescent light model $M_L^Q$ in FIG. 13D. The relative fluid flow model $M_{Fr}^Q$ is indicated in relation to the mean flow velocity $$v_R = v_{average} = \frac{\int_Q M_F^Q(x)dx}{\int_Q dx}$$

of the fluid flow model $M_F^Q$. The corrected flow velocity $v_{corrected}$ in the form of the mean flow velocity $\overline{v_{average}}$ to be expected in the portion of the blood vessel can be determined from the flow velocity $v_{observed}$ observed in the portion of the blood vessel, using the relative fluid flow model $M_{Fr}^Q$ and the fluorescent light model $M_L^Q$, as follows:

$$v_{corrected} := \overline{v_{average}} = v_{observed} \cdot k_{average}$$

with the correction factor $$k_{average} := \frac{1}{\int_Q M_{Fr}^Q(x) \, M_L^Q(x)dx}.$$

For the relative fluid flow model $M_{Fr}^Q$ shown in FIG. 9B at the reference flow velocity $v_{average}$ and the fluorescent light model $M_{Fr}^Q$ shown in the graph 131 of FIG. 10, in respect of a diameter D of 3 mm for example, the correction factor $k_{average}=0.68$.

To save computing time, the correction factor $k\_v_R$ for different model parameters, e.g. for different diameters D of the flow channel 94, is calculated in advance and stored in a look-up table (LUT).

FIG. 14A shows a horizontal cross section of a portion 90$_i$ of a blood vessel 88.

FIG. 14B shows a calculation of the velocity $v_{observed}$, observed in the portion of the blood vessel, in the portion 90$_i$ of the blood vessel 88. For this purpose, a time development 160 of the intensity I in the first sector $A_1$ and a time development 162 of the intensity in the second sector $A_2$ over the majority of the provided images 80$_1$, 80$_2$, 80$_3$, 80$_4$, . . . is considered. For this purpose, the intensity values I(t) are averaged over the pixels in the respective sector $A_1$, $A_2$. A continuous function 106 in the form of a gamma function is fitted to the discrete intensity values I(t) in order to obtain intermediate values and, even at a low image rate, to be able to determine as accurately as possible the velocity $v_{observed}$ observed in the portion of the blood vessel.

The time offset of the two curves, which is determined here by cross-correlation, then corresponds to the transit time τ. The blood flow direction can also be derived from this offset. It should be noted that the time offset of the two curves can in principle also be determined by averaging time offsets of distinct features of the two curves instead of using cross-correlation.

From the transit time τ, the length L and the diameter D of the portion 90$_i$ of the blood vessel 88 and the correction factor $k\_v_R$, the blood volume flow $I_{Bi}$ can then be calculated as $$I_{Bi} = \dot{V} = \left(\frac{D}{2}\right)^2 \pi \frac{Lk}{\tau} = \left(\frac{D}{2}\right)^2 \pi v_{observed} k\_v_R.$$

The blood volume flow $I_{Bi}$ is given a confidence interval depending on the length L, the diameter D, the correction factor k, the transit time τ and the shape of the center line 98, for which purpose the angle of the partial sections of the center line to grid lines of a grid of the image sensor of the image acquisition device is also taken into account.

The uncertainty is calculated according to DIN 1319 as the propagation of non-correlated input uncertainties without assuming a normal distribution.

Figure 15:
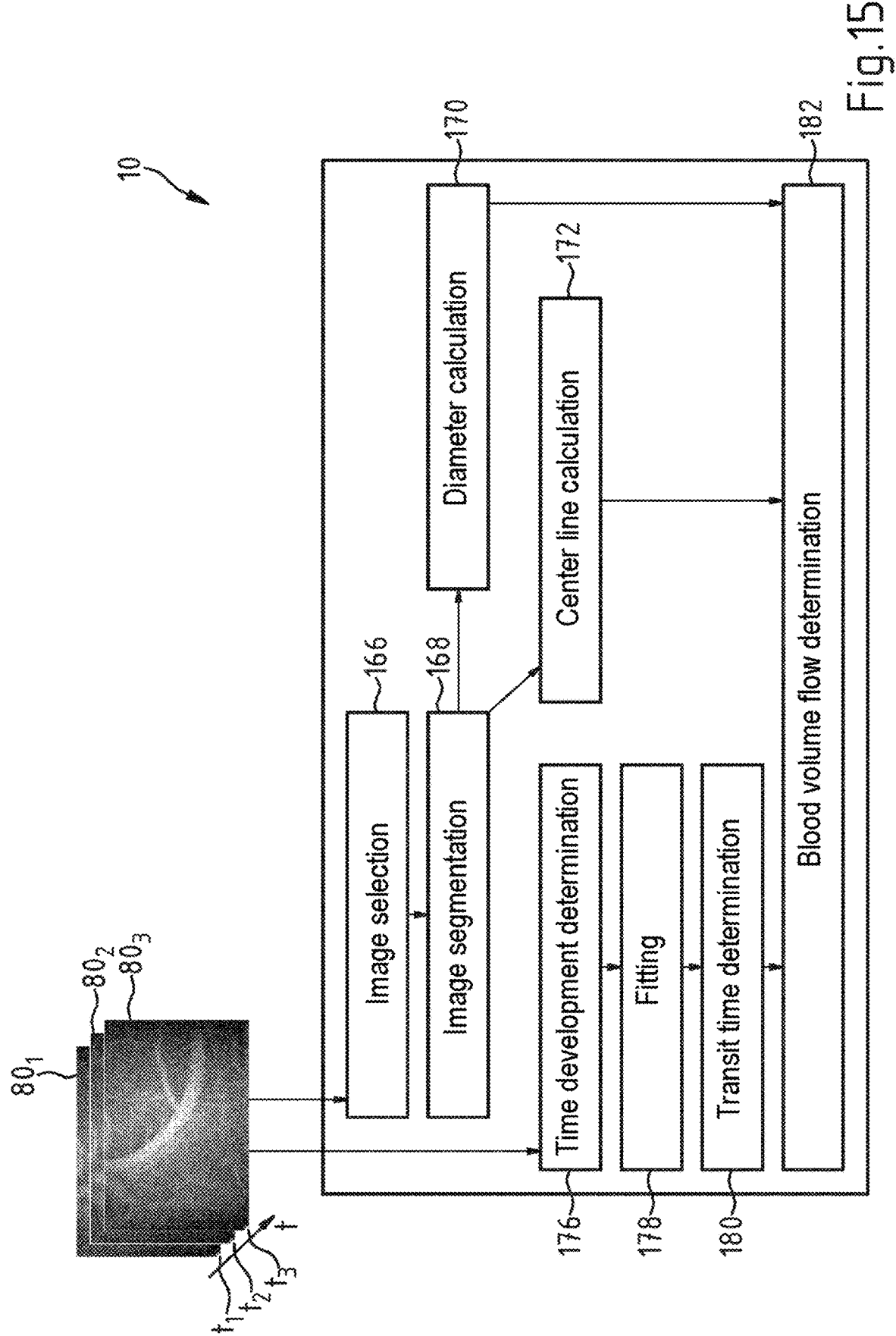
FIG. 15 shows an exemplary embodiment with method steps for determining a blood volume flow in a sector of a blood vessel in an operating region.

FIG. 15 shows a flow chart for an embodiment of the method 10 for determining the blood volume flow $I_{Bi}$ in a portion 90$_i$ of a blood vessel 88 in an operating region 36 of a patient based on a plurality of provided images 80$_1$, 80$_2$, 80$_3$, 80$_4$, . . . . In a step of image selection 166, an image is selected from the provided images 80$_1$, 80$_2$, 80$_3$, 80$_4$, . . . . The selected image is segmented in a step of image segmentation 168. A diameter D is determined from the segmentation 96 in a step of diameter calculation 170. In addition, a center line 98 of the portion 90$_i$ of the blood vessel 88 and the length L of said center line 98 are determined in a step of center line calculation 172.

The time development 160, 162 of the intensity in the first and second portion is determined in a step of time development determination 176. In a fitting step 178, a continuous function 106 is fitted to the time developments 160, 162. The transit time τ is calculated, in a step of transit time determination 180, from the offset between the continuous functions 106 adapted to the time developments 160, 162. Finally, in a step of blood volume flow determination 182, the blood volume flow $I_{Bi}$ is determined from the determined data.

Figure 16:
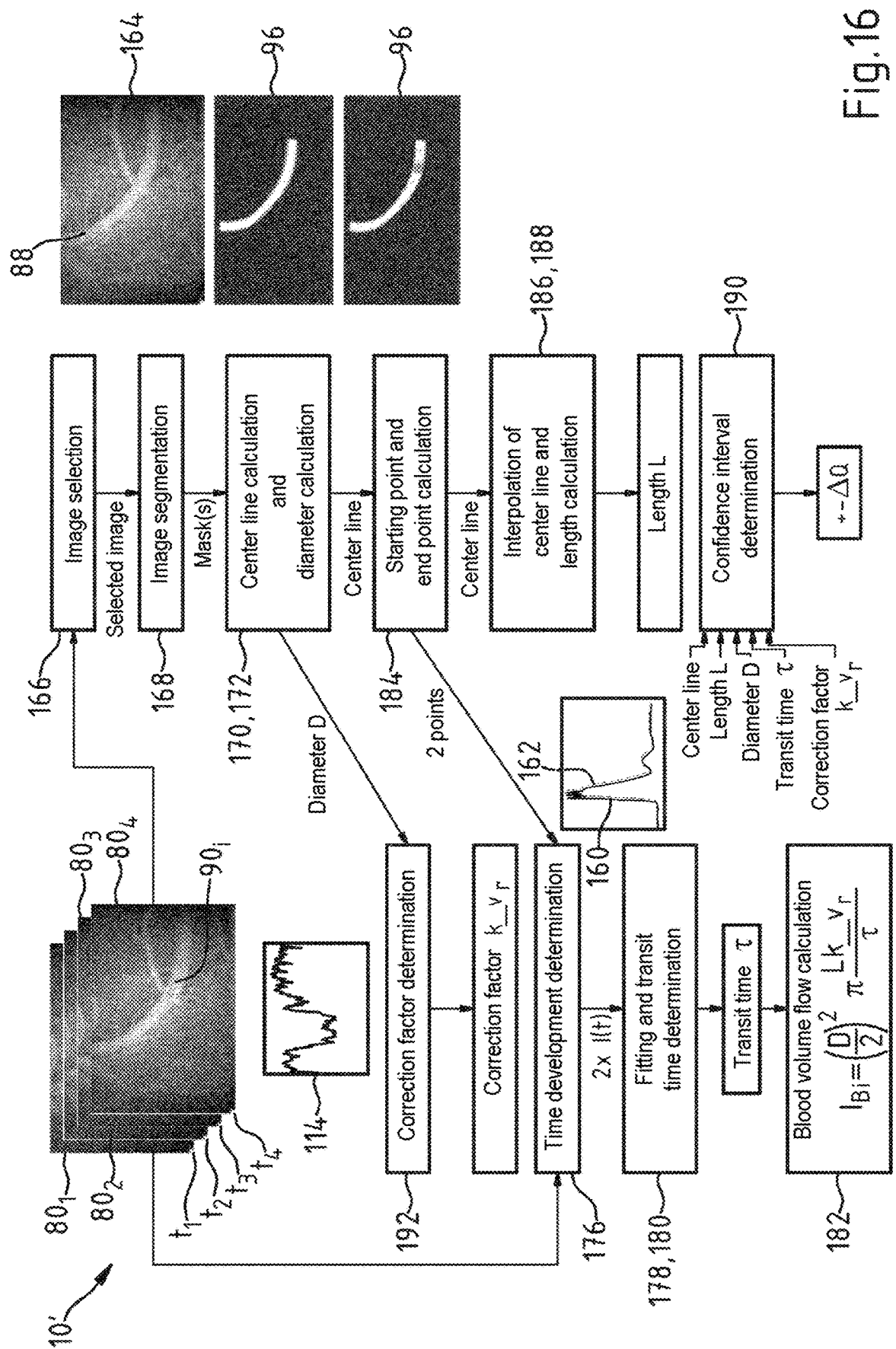
FIG. 16 shows an exemplary embodiment with method steps for determining a blood volume flow in a sector of a blood vessel in an operating region.

FIG. 16 shows a flow chart for a further embodiment of the method 10' for determining the blood volume flow $I_{Bi}$ in a portion 90$_i$ of a blood vessel 88 in an operating region 36. An image acquisition device 64 is used to record a video of the operating region 36 under illumination light 46, such that the fluorescent dye is visible. The video consists of a plurality of images 80$_1$, 80$_2$, 80$_3$, 80$_4$, . . . , which are based on fluorescence light in the form of illumination light 46 with wavelengths lying within a fluorescence spectrum of the fluorophore and which show the portion 90$_i$ of the blood vessel 88 at different recording times. From the plurality of images 80$_1$, 80$_2$, 80$_3$, 80$_4$, . . . , a selected image 164 is determined in a step of image selection 166, the selected image 164 having the maximum number of color-saturated pixels of all the provided images 80$_1$, 80$_2$, 80$_3$, 80$_4$, . . . . Using an image segmentation method, in a step of image segmentation 168, the portion 90$_i$ of the blood vessel 88 in the selected image 164 is determined. In a center line calculation 172, the segmentation 96 is used to calculate a center line 98 of the portion 90$_i$ of the blood vessel 88. Based on the segmentation 96 of the portion 90$_i$ of the blood vessel 88 and on the center line 98, the diameter D is calculated in a diameter calculation 170. In a starting point and end point calculation 184, a starting point $P_1$ and an end point $P_2$ are determined on the center line. In an interpolation step 186, the center line 98 is interpolated, e.g. in sections with a Bezier spline, and, based on the interpolated center line 98, the length L of the portion 90$_i$ of the blood vessel 88 is determined in a length calculation 188. Using the center line 98, the curve 114 of the intensity profile I(x) orthogonal to the center line 98, and the segmentation 96 of the portion 90$_i$ of the blood vessel 88, a diameter D of the portion 90$_i$ of the blood vessel 88 is determined in a diameter calculation 170. Then, in a correction factor determination 192, a correction factor $k\_v_r$ for the diameter D is determined using a look-up table. Moreover, a characteristic transit time τ is determined as a time interval for a propagation of the fluorophore through the portion 90$_i$ of the blood vessel 88. For this purpose, in a time development determination 176 at two different sectors $A_1$, $A_2$, where $A_1$ contains the starting point $P_1$ and $A_2$ contains the end point $P_2$, a time development 160, 162 of the image brightness is determined. For this purpose, a mean value of the intensities in the respective sector $A_1$, $A_2$ over time is considered. A continuous function 106, e.g. a gamma function, is fitted, in a step of fitting 178, to the resulting measured values of the time development 160, 162. In a transit time determination 180, the transit time τ is calculated from the time offset of the resulting curves. The blood volume flow $I_{Bi}$ finally results from the length L and the diameter D of the portion 90$_i$ of the blood vessel 88 and also the transit time τ and the correction factor $k\_v_r$ in a blood volume flow determination 182. In addition, a confidence interval is determined in a confidence interval determination 190 based on the calculated parameters.

In summary, the following in particular should be noted: The invention relates to a computer-implemented method 10 for determining the blood volume flow IBI through a portion 90$_i$, i=1, 2, 3, . . . of a blood vessel 88 in an operating region 36 using a fluorophore, in which a plurality of images 80$_1$, 80$_2$, 80$_3$, 80$_4$, . . . are provided, which are based on fluorescent light in the form of light having wavelengths lying within a fluorescence spectrum of the fluorophore, and which show the portion $90_i$ of the blood vessel 88 at different recording times $t_1, t_2, t_3, t_4, \ldots$, in which, by processing the provided images $80_1, 80_2, 80_3, 80_4, \ldots$, a diameter D and a length L of the portion $90_i$ of the blood vessel 88 and also a time interval for a propagation of the fluorophore through the portion $90_i$ of the blood vessel 88 are determined, which time interval describes a characteristic transit time $\tau$ for the fluorophore in the portion $90_i$ of the blood vessel 88, wherein a blood vessel model $M_B^Q$ for the portion $90_i$ of the blood vessel 88 is processed, which blood vessel model describes the portion $90_i$ of the blood vessel 88 as a flow channel 94 having a length L, having a wall 95 with a wall thickness d, and having a free cross section Q, wherein at least one of the provided images $80_1, 80_2, 80_3, 80_4, \ldots$ is processed, which processes a fluid flow model $M_F^Q$ to the blood vessel model $M_B^Q$, which describes a local flow velocity 122 at different positions over the free cross section Q of the flow channel 94 in the blood vessel model $M_B^Q$, which processes a fluorescent light model $M_L^Q$ which describes a spatial probability density for the intensity of the remitted light at different positions over the free cross section Q of the flow channel 94 in the blood vessel model $M_B^Q$, which light is emitted by a fluid, which is mixed with fluorophore and flows through the free cross section Q of the flow channel 94 in the blood vessel model $M_B^Q$, when said fluid is irradiated with fluorescence excitation light, and in which the blood volume flow $I_{BI}$ is determined as a fluid flow guided through the flow channel 94 in the blood vessel model $M_B^Q$, which fluid flow is calculated from the length L and the diameter D of the portion $90_i$ of the blood vessel 88 and from the characteristic transit time $\tau$ for the fluorophore in the portion $90_i$ of the blood vessel 88, based on the fluid flow model $M_F^Q$ and the fluorescent light model $M_L^Q$.

LIST OF REFERENCE SIGNS 10, 10' Method
12 Surgical microscope
14 System for determining the blood volume flow
20 Microscope main objective
22 Microscope main body
24 Magnification system
26 Left observation beam path
28 Right observation beam path
30 Binocular tube
32 Eyepiece lens
34 Tube lens
36 Operating region
37 Brain
38 Left observer eye
40 Right observer eye
42 Illumination device
44 Illumination beam path
46 Illumination light
48 Xenon light source
50 Lens element
52 Light guide
54 Illumination objective
56 Illumination filter
59 Arrow
60 Observation filter for the left observation beam path
62 Observation filter for the right observation beam path
64 Image acquisition device
66 Output coupling beam splitter
68 Optical axis
70 Image sensor
71 Region
72 Computer unit
74 Input unit
76 Program memory
78 Screen
$80_1$ Image 1
$80_2$ Image 2
$80_3$ Image 3
$80_4$ Image 4
82 Display
84 Lens element
86 Beam splitter
88 Blood vessel
89 Branch
90, $90_i$, i=1, 2, 3, . . . Portion
91 Cylinder axis
92 Arrow
93 Arrow
94 Flow channel
95 Wall
96 Segmentation
$97_i$ Image portion
98 Center line
99 Center line portion
100 Post-processed center line
102 Discretized center line
104 Polygonal chain
106 Continuous functions
108 Pixel neighborhood
110 L-shaped connection structure
112 Diagonal connection structure
114 Curve
115 Intensity value
116 Flow channel edge point
120 Flow profile
122 Local flow velocity
124 Relative flow profile
126 Local relative flow velocity
127 Photon
128 Layer model
129 Layer
130 Layer boundary
131 Graph
132 Initialization
134 Photon introduction
136 Query
138 Step size calculation
140 Boundary distance determination
142 Query
144 Photon adaptation
146 Query
148 Weight absorption
150 Scatter calculation
152 Query
154 Photon end
158 Program end
160 Time development of the intensity I(t) in the first portion
162 Time development of the intensity I(t) in the second portion
164 Selected image
166 Image selection
168 Image segmentation
170 Diameter calculation
172 Center line calculation
176 Time development determination
178 Fitting
180 Transit time determination
182 Blood volume flow determination 184 Starting point and end point calculation
186 Interpolation
188 Length calculation
190 Confidence interval determination
192 Correction factor determination
$I_B$ Blood volume flow through blood vessel
$I_{Bi}$ Blood volume flow through i-th portion of a blood vessel
ICG Indocyanine green
$M_B^Q$ Blood vessel model
$M_F^Q$ Fluid flow model
$M_{Fr}^Q$ Relative fluid flow model
$M_L^Q$ Fluorescent light model
$t_1, t_2, t_3, t_4$ Recording times
L Length of the portion of the blood vessel
Q Cross section of the flow channel
A Cylinder axis
D Diameter
$D_L$ Local diameter
G Overall diameter
$G_L$ Local overall diameter
d Wall thickness
$d_L$ Local wall thickness
$P_1$ Starting point
$P_2$ End point
$v_R$ Reference flow velocity
$A_1$ First sector
$A_2$ Second sector
τ Transit time
$k\_v_R$ Correction factor for reference flow velocity $v_R$
$v_{model}$ Flow velocity observed in the blood vessel model
$v_{observed}$ Flow velocity observed in the portion of the blood vessel

The invention claimed is:

1. A computer-implemented method for determining blood volume flow through a portion of a blood vessel in an operating region using a fluorophore;
   in which a plurality of images are provided, which are based on fluorescent light in a form of light having wavelengths lying within a fluorescence spectrum of the fluorophore, and which show the portion of the blood vessel at different recording times;
   in which, by processing the provided images, a diameter and a length of the portion of the blood vessel and a time interval for a propagation of the fluorophore through the portion of the blood vessel are determined, which time interval describes a characteristic transit time for the fluorophore in the portion of the blood vessel;
   in which a blood vessel model, which describes the portion of the blood vessel as a flow channel having a length, having a wall with a wall thickness, and having a free cross section, on at least one of the provided images is adapted to at least one of the images provided by means of image processing;
   in which a fluid flow model for the adapted blood vessel model is provided, which fluid flow model describes a local flow velocity at different positions over the free cross section of the flow channel in the adapted blood vessel model, the method comprising:
   providing a fluorescent light model that describes a spatial probability density for the intensity of the remitted light at different positions over the free cross section of the flow channel in the adapted blood vessel model, which light is emitted by a fluid, which is mixed with fluorophore and flows through the free cross section of the flow channel in the adapted blood vessel model, when said fluid is irradiated with fluorescence excitation light; and
   determining the blood volume flow as a fluid flow guided through the flow channel in the adapted blood vessel model, which fluid flow is calculated from the length and the diameter of the portion of the blood vessel and from the characteristic transit time for the fluorophore in the portion of the blood vessel, using the fluid flow model provided and the fluorescent light model provided.

2. The computer-implemented method as claimed in claim 1, wherein the plurality of images are acquired using an image acquisition device, wherein, during the determination of the blood volume flow, parameters of the image acquisition device, of the blood vessel model, of the fluid flow model and of the fluorescent light model are not changed.

3. The computer-implemented method as claimed in claim 1, wherein the blood vessel model is a hollow cylinder with length, diameter and wall thickness, and/or wherein the fluid flow model describes a laminar fluid flow through the flow channel of the blood vessel model.

4. The computer-implemented method as claimed in claim 1, wherein the fluorescent light model is based on a simulation of an irradiation of the blood vessel model with fluorescence excitation light, in which photons are assumed to be particles scattered at scattering centers, the scattering centers in the flow channel and in the wall of the blood vessel model each having a characteristic scattering center distribution.

5. The computer-implemented method as claimed in claim 4, wherein the archetype of the fluorescent light model corresponds to a chord of the free cross section of the blood vessel model which represents the penetration depth of the photons into the blood vessel model upon irradiation with fluorescence excitation light, and wherein the fluorescent light model represents the penetration depth on the proportion of the photons remitted from the blood vessel model, the maximum penetration depth of which photons in the blood vessel model corresponds to the value x during the simulation.

6. The computer-implemented method as claimed in claim 1, wherein the fluid flow model is a relative fluid flow model which describes a local relative flow velocity at different positions over the free cross section of the flow channel in the blood vessel model in relation to a reference flow velocity.

7. The computer-implemented method as claimed in claim 6, wherein the fluid flow guided through the flow channel in the blood vessel model is calculated by using the relative fluid flow model to the reference flow velocity and the fluorescent light model to determine a correction factor, and by using the length of the portion of the blood vessel and the characteristic transit time for the fluorophore in the portion of the blood vessel to determine a fluorophore propagation speed which, by means of the correction factor, is corrected to a value corresponding to the reference flow velocity.

8. The computer-implemented method as claimed in claim 7, wherein the correction factor, as the inverse of the expected value of the relative flow velocities in the relative fluid flow model, dependent on the spatial probability density described by the fluorescent light model for the intensity of the remitted light at different positions over the free cross section of the flow channel in the blood vessel model, is determined according to the following equation:

$$k\_v_R = \frac{1}{\int_Q M_{Fr}^Q(x) M_L^Q(x) dx}.$$

9. The computer-implemented method as claimed in claim 1, wherein the length of the portion of the blood vessel and/or the diameter of the portion of the blood vessel is determined, on the basis of a center line of the portion of the blood vessel, in at least one of the provided images.

10. The computer-implemented method as claimed in claim 9, wherein the center line of the portion of the blood vessel is ascertained:
- by determining pixels on the center line of the portion of the blood vessel by processing the provided images,
- by determining a polygonal chain from the pixels of the center line,
- by minimizing the length of the polygonal chain by adapting connection structures of the pixels along the center line on the basis of their pixel neighborhoods, and
- by fitting continuous functions to the minimized polygonal chain.

11. The computer-implemented method as claimed in claim 1, wherein:
- the fluid flow model and the fluorescent light model describe a local sector of the blood vessel model, such that the archetype of the fluid flow model and of the fluorescent light model represents a partial region of the free cross section of the blood vessel model;
and/or
- the length, the diameter, a center line of the portion of the blood vessel, the blood vessel model, the fluid flow model and/or the fluorescent light model are determined using a criterion relating to the intensity as a measure of the image brightness of the pixels of the selected image,
and/or
- the transit time is determined from the offset of a time development of the image brightness at at least two different sectors of the portion of the blood vessel by processing the provided images, and in that a continuous function is in each case fitted to the time development of the image brightness at the different sectors of the portion of the blood vessel;
and/or
- for the calculated blood volume flow in the portion of the blood vessel, a confidence interval based on the diameter and/or the length of the portion of the blood vessel and/or the transit time and/or a correction factor and/or the blood vessel model and/or the fluid flow model and/or the fluorescent light model and/or the shape of a center line of the portion of the blood vessel is determined on the basis of error simulations;
and/or
- in that the portion of the blood vessel is determined by processing the provided images using an image segmentation method.

12. The computer-implemented method as claimed in claim 1, wherein the width of the flow channel and the wall thickness of the wall of the blood vessel model are determined based on a criterion relating to a curve of the intensity profile orthogonal to a center line of the portion of the blood vessel in one or more of the provided images.

13. The computer-implemented method as claimed in claim 12, wherein the criterion relating to the curve of the intensity profile takes into account a minimum of the curvature of the curve of the intensity profile orthogonal to a center line of the portion of the blood vessel.

14. A computer-implemented method for determining the blood volume flow through a blood vessel in an operating region using a fluorophore, in which the blood vessel is divided into several portions and the blood volume flow in the portions is determined as claimed in claim 1, with the proviso that, at a branch of the blood vessel, the sum of the blood volume flows to the branch corresponds to the sum of the blood volume flows from the branch.

15. A computer program having a program code for carrying out all method steps specified in claim 1, wherein the computer program is stored in a non-transitory computer unit.

16. A surgical system for determining the blood volume flow through a portion of a blood vessel in an operating region using a fluorophore, the surgical system comprising:
- an illumination device for providing fluorescence excitation light for the operating region;
- an image acquisition device for providing a plurality of images, which are based on light having wavelengths lying within a fluorescence spectrum of the fluorophore, and which show the portion of the blood vessel at different times; and
- a computer unit containing a computer program as claimed in claim 15.

* * * * *